United States Patent
Moos et al.

(10) Patent No.: US 8,523,809 B2
(45) Date of Patent: Sep. 3, 2013

(54) DEVICE FOR SHIELDING A SHARP TIP OF A CANNULA AND METHOD OF USING THE SAME

(75) Inventors: Kimberly A. Moos, Florissant, MO (US); David Rork Swisher, St. Charles, MO (US)

(73) Assignee: Covidien AG (CH)

( * ) Notice: Subject to any disclaimer, the term of this patent is extended or adjusted under 35 U.S.C. 154(b) by 574 days.

(21) Appl. No.: 12/770,204

(22) Filed: Apr. 29, 2010

(65) Prior Publication Data

US 2010/0217152 A1 Aug. 26, 2010

Related U.S. Application Data

(62) Division of application No. 11/179,143, filed on Jul. 11, 2005, now Pat. No. 7,731,692.

(51) Int. Cl.
| | |
|---|---|
| *A61M 5/00* | (2006.01) |
| *A61B 10/00* | (2006.01) |
| *A61B 17/14* | (2006.01) |
| *A61B 17/32* | (2006.01) |

(52) U.S. Cl.
USPC .............................. 604/110; 600/567; 606/184

(58) Field of Classification Search
USPC .................. 604/110, 164.01, 164.08, 170.01, 604/170.02, 197, 198; 600/562, 566, 567, 600/583; 606/167, 181, 184
See application file for complete search history.

(56) References Cited

U.S. PATENT DOCUMENTS

| | | | |
|---|---|---|---|
| 1,115,561 A | 11/1914 | Northey | |
| 1,436,707 A | 11/1922 | Gaschke | |
| 1,518,531 A | 12/1924 | Lung | |
| 2,219,605 A | 6/1938 | Turkel | |
| 2,854,976 A | 10/1958 | Heydrich | |
| 3,254,533 A | 6/1966 | Tongret | |
| 3,539,034 A | 11/1970 | Tafeen | |
| 3,610,240 A | 10/1971 | Harautuneian | |
| 3,681,991 A | 8/1972 | Eberly | |
| 3,729,998 A | 5/1973 | Mueller et al. | |
| 3,822,598 A | 7/1974 | Hunter et al. | |
| 3,884,230 A | 5/1975 | Wulff | |
| 3,890,971 A | 6/1975 | Leeson et al. | |
| 3,893,058 A | 7/1975 | Keith | |
| 3,893,445 A | 7/1975 | Hofsess | |
| 3,904,033 A | 9/1975 | Haerr | |
| 3,915,003 A | 10/1975 | Adams | |
| 3,946,613 A | 3/1976 | Silver | |
| 3,976,070 A | 8/1976 | Dumont | |
| 4,008,614 A | 2/1977 | Turner et al. | |
| 4,010,737 A | 3/1977 | Vilaghy et al. | |
| 4,026,287 A | 5/1977 | Haller | |

(Continued)

FOREIGN PATENT DOCUMENTS

| | | |
|---|---|---|
| DE | 3805567 | 8/1989 |
| EP | 1 358 846 | 11/2003 |

(Continued)

*Primary Examiner* — Nicholas Lucchesi
*Assistant Examiner* — Nathan R Price
(74) *Attorney, Agent, or Firm* — Lisa E. Winsor, Esq.

(57) ABSTRACT

A safety device for shielding a sharp tip of a tubular needle includes a shaft sized and shaped for being received into the passage of the tubular needle through a first end of the passage and extending to a second end of the passage. A shield is associated with the shaft and is constructed for receiving and substantially shielding the sharp tip of the needle. A catch is associated with the shaft. The catch prevents the withdrawal of the shaft from the passage of the needle when the shield is shielding the sharp tip of the needle.

19 Claims, 12 Drawing Sheets

(56) References Cited

U.S. PATENT DOCUMENTS

| | | |
|---|---|---|
| 4,099,518 A | 7/1978 | Baylis et al. |
| D249,475 S | 9/1978 | Turner et al. |
| 4,112,762 A | 9/1978 | Turner et al. |
| 4,139,009 A | 2/1979 | Alvarez |
| 4,142,517 A | 3/1979 | Slavropoulos et al. |
| 4,143,853 A | 3/1979 | Abramson |
| 4,160,450 A | 7/1979 | Doherty |
| 4,163,446 A | 8/1979 | Jamshidi |
| 4,177,797 A | 12/1979 | Baylis et al. |
| 4,183,248 A | 1/1980 | West |
| D255,997 S | 7/1980 | Maeda |
| 4,211,214 A | 7/1980 | Chikashige |
| 4,256,119 A | 3/1981 | Gauthier |
| 4,258,713 A | 3/1981 | Wardlaw |
| 4,258,722 A | 3/1981 | Sessions et al. |
| 4,262,676 A | 4/1981 | Jamshidi |
| 4,266,543 A | 5/1981 | Blum |
| 4,266,555 A | 5/1981 | Jamshidi |
| 4,314,565 A | 2/1982 | Lee |
| 4,356,828 A | 11/1982 | Jamshidi |
| 4,392,859 A | 7/1983 | Dent |
| 4,403,617 A | 9/1983 | Tretinyak |
| 4,425,120 A | 1/1984 | Sampson et al. |
| 4,438,884 A | 3/1984 | O'Brien et al. |
| 4,469,109 A | 9/1984 | Mehl |
| 4,482,348 A | 11/1984 | Dent |
| 4,487,209 A | 12/1984 | Mehl |
| 4,513,754 A | 4/1985 | Lee |
| 4,543,966 A | 10/1985 | Islam et al. |
| 4,572,365 A | 2/1986 | Bruno et al. |
| 4,573,976 A | 3/1986 | Sampson et al. |
| 4,613,329 A | 9/1986 | Bodicky |
| 4,619,271 A | 10/1986 | Burger et al. |
| 4,630,616 A | 12/1986 | Tretinyak |
| 4,631,057 A | 12/1986 | Mitchell |
| 4,639,249 A | 1/1987 | Larson |
| 4,642,785 A | 2/1987 | Packard et al. |
| 4,643,199 A | 2/1987 | Jennings |
| 4,643,200 A | 2/1987 | Jennings |
| 4,655,226 A | 4/1987 | Lee |
| 4,664,654 A | 5/1987 | Strauss |
| 4,676,783 A | 6/1987 | Jagger et al. |
| 4,681,567 A | 7/1987 | Masters |
| 4,693,708 A | 9/1987 | Wanderer |
| 4,695,274 A | 9/1987 | Fox |
| D292,493 S | 10/1987 | King |
| D292,494 S | 10/1987 | King |
| D293,215 S | 12/1987 | Bruno et al. |
| 4,723,943 A | 2/1988 | Spencer |
| 4,725,267 A | 2/1988 | Vaillancourt |
| 4,728,320 A | 3/1988 | Chen |
| 4,735,619 A | 4/1988 | Sperry |
| 4,737,144 A | 4/1988 | Choksi |
| 4,738,663 A | 4/1988 | Bogan |
| 4,741,627 A | 5/1988 | Fukui |
| 4,743,233 A | 5/1988 | Schneider |
| 4,747,831 A | 5/1988 | Kulh |
| 4,747,836 A | 5/1988 | Luther |
| 4,747,837 A | 5/1988 | Hauck |
| 4,752,290 A | 6/1988 | Schramm |
| 4,762,516 A | 8/1988 | Lulher |
| 4,770,655 A | 9/1988 | Haber et al. |
| 4,772,272 A | 9/1988 | McFarland |
| 4,775,363 A | 10/1988 | Sandsdalen |
| 4,781,684 A | 11/1988 | Trenner |
| 4,781,692 A | 11/1988 | Jagger et al. |
| 4,785,826 A | 11/1988 | Ward |
| 4,790,329 A | 12/1988 | Simon |
| 4,790,827 A | 12/1988 | Haber et al. |
| 4,790,828 A | 12/1988 | Dombrowski |
| 4,793,363 A | 12/1988 | Ausherman et al. |
| 4,795,432 A | 1/1989 | Karczmer |
| 4,804,371 A | 2/1989 | Vaillancourt |
| 4,804,372 A | 2/1989 | Laico |
| 4,810,248 A | 3/1989 | Masters et al. |
| 4,813,426 A | 3/1989 | Haber et al. |
| 4,816,022 A | 3/1989 | Poncy |
| D300,728 S | 4/1989 | Ross |
| 4,819,659 A | 4/1989 | Silar |
| 4,820,275 A | 4/1989 | Haber et al. |
| 4,826,488 A | 5/1989 | Nelson |
| 4,826,490 A | 5/1989 | Byrne et al. |
| 4,826,491 A | 5/1989 | Schramm |
| 4,834,718 A | 5/1989 | McDonald |
| 4,838,280 A | 6/1989 | Haaga |
| 4,838,282 A | 6/1989 | Strasser et al. |
| 4,842,586 A | 6/1989 | Hogan |
| 4,846,809 A | 7/1989 | Sims |
| 4,900,307 A | 2/1990 | Kulli |
| 4,904,242 A | 2/1990 | Kulli |
| 4,906,235 A | 3/1990 | Roberts |
| 4,909,793 A | 3/1990 | Vining |
| 4,911,694 A | 3/1990 | Dolan |
| 4,911,706 A | 3/1990 | Levitt |
| 4,915,702 A | 4/1990 | Haber |
| D307,558 S | 5/1990 | Messina et al. |
| 4,922,602 A | 5/1990 | Mehl |
| 4,927,414 A | 5/1990 | Kulli |
| 4,929,241 A | 5/1990 | Kulli |
| 4,931,044 A | 6/1990 | Beiter |
| 4,935,013 A | 6/1990 | Haber et al. |
| 4,943,283 A | 7/1990 | Hogan |
| 4,944,725 A | 7/1990 | McDonald |
| 4,950,250 A | 8/1990 | Haber |
| 4,952,207 A | 8/1990 | Lemieux |
| 4,955,866 A | 9/1990 | Corey |
| 4,958,625 A | 9/1990 | Bates et al. |
| 4,960,412 A | 10/1990 | Fink |
| 4,964,854 A | 10/1990 | Luther |
| 4,966,587 A | 10/1990 | Baumgart |
| 4,969,554 A | 11/1990 | Sawaya |
| 4,978,344 A | 12/1990 | Dombrowski |
| 4,986,279 A | 1/1991 | O'Neill |
| 4,994,041 A | 2/1991 | Dombrowski |
| 5,005,585 A | 4/1991 | Mazza |
| 5,012,818 A | 5/1991 | Joishy |
| 5,013,304 A | 5/1991 | Russell et al. |
| 5,031,634 A | 7/1991 | Simon |
| 5,036,860 A | 8/1991 | Leigh et al. |
| 5,047,044 A | 9/1991 | Smith et al. |
| 5,049,136 A | 9/1991 | Johnson |
| 5,051,109 A | 9/1991 | Simon |
| 5,053,017 A | 10/1991 | Chamuel |
| 5,057,085 A | 10/1991 | Kopans |
| 5,059,180 A | 10/1991 | McLees |
| 5,085,648 A | 2/1992 | Purdy et al. |
| 5,092,851 A | 3/1992 | Ragner |
| 5,102,394 A | 4/1992 | Lasaitis |
| 5,108,374 A | 4/1992 | Lemieux |
| 5,126,090 A | 6/1992 | Egolf et al. |
| 5,127,916 A | 7/1992 | Spencer et al. |
| 5,133,727 A | 7/1992 | Bales et al. |
| 5,135,504 A | 8/1992 | McLees |
| 5,147,327 A | 9/1992 | Johnson |
| 5,154,703 A | 10/1992 | Bonaldo |
| 5,158,565 A * | 10/1992 | Marcadis et al. ............. 606/185 |
| 5,171,229 A | 12/1992 | McNeil et al. |
| 5,172,702 A | 12/1992 | Leigh et al. |
| 5,176,256 A | 1/1993 | Sawaya |
| 5,183,468 A | 2/1993 | McLees |
| 5,195,533 A | 3/1993 | Chin et al. |
| 5,195,985 A | 3/1993 | Hall |
| 5,213,115 A | 5/1993 | Zytkovicz et al. |
| 5,215,525 A | 6/1993 | Sturman |
| 5,215,528 A | 6/1993 | Purdy et al. |
| 5,215,533 A | 6/1993 | Robb |
| 5,217,438 A | 6/1993 | Davis |
| 5,228,451 A | 7/1993 | Bales et al. |
| 5,257,632 A | 11/1993 | Turkel et al. |
| 5,279,306 A | 1/1994 | Mehl |
| 5,279,563 A | 1/1994 | Brucker et al. |
| 5,279,591 A | 1/1994 | Simon |
| 5,282,477 A | 2/1994 | Bauer |
| 5,295,977 A | 3/1994 | Cohen et al. |

| | | | | | |
|---|---|---|---|---|---|
| 5,304,136 A | 4/1994 | Erskine | 5,569,217 A | 10/1996 | Luther |
| 5,312,359 A | 5/1994 | Wallace | 5,569,299 A | 10/1996 | Dill et al. |
| 5,314,406 A | 5/1994 | Arias et al. | 5,570,783 A | 11/1996 | Thome et al. |
| 5,316,013 A | 5/1994 | Striebel, II et al. | 5,573,008 A | 11/1996 | Robinson et al. |
| 5,320,635 A | 6/1994 | Smith | 5,573,510 A | 11/1996 | Isaacson |
| 5,322,517 A | 6/1994 | Sircom et al. | 5,578,015 A | 11/1996 | Robb |
| 5,324,288 A | 6/1994 | Billings et al. | 5,584,809 A | 12/1996 | Gaba |
| 5,328,482 A | 7/1994 | Sircom et al. | 5,584,810 A | 12/1996 | Brimhall |
| 5,331,971 A | 7/1994 | Bales et al. | 5,584,818 A | 12/1996 | Morrison |
| 5,331,972 A | 7/1994 | Wadhwani et al. | 5,586,990 A | 12/1996 | Hahnen et al. |
| 5,334,158 A | 8/1994 | McLees | 5,591,202 A | 1/1997 | Slater et al. |
| 5,338,311 A | 8/1994 | Mahurkar | 5,595,186 A | 1/1997 | Rubinstein et al. |
| 5,338,314 A | 8/1994 | Ryan | 5,599,310 A | 2/1997 | Bogert |
| 5,341,816 A | 8/1994 | Allen | 5,601,536 A | 2/1997 | Crawford et al. |
| 5,344,408 A | 9/1994 | Partika | 5,601,585 A | 2/1997 | Banik et al. |
| 5,348,022 A | 9/1994 | Leigh et al. | 5,601,599 A | 2/1997 | Nunez |
| 5,348,544 A | 9/1994 | Sweeney et al. | 5,611,781 A | 3/1997 | Sircom et al. |
| 5,356,421 A | 10/1994 | Caslro | 5,615,690 A | 4/1997 | Giurtino et al. |
| 5,357,974 A | 10/1994 | Baldridge | 5,616,135 A | 4/1997 | Thorne et al. |
| 5,368,045 A | 11/1994 | Clement et al. | 5,623,969 A | 4/1997 | Raines |
| 5,368,046 A | 11/1994 | Scarfone et al. | 5,624,459 A | 4/1997 | Kortenbach et al. |
| 5,370,623 A | 12/1994 | Kreamer | 5,630,506 A | 5/1997 | Thorne et al. |
| D354,921 S | 1/1995 | Narayanan | 5,630,837 A | 5/1997 | Crowley |
| 5,385,151 A | 1/1995 | Scarfone et al. | 5,632,555 A | 5/1997 | Gregory |
| 5,385,570 A | 1/1995 | Chin et al. | 5,634,473 A | 6/1997 | Goldenberg et al. |
| 5,389,104 A | 2/1995 | Hahnen et al. | 5,643,307 A | 7/1997 | Turkel et al. |
| 5,389,106 A | 2/1995 | Tower | 5,656,031 A | 8/1997 | Thorne et al. |
| 5,394,885 A | 3/1995 | Francese | 5,662,610 A | 9/1997 | Sircom |
| 5,395,375 A | 3/1995 | Turkel et al. | 5,666,965 A | 9/1997 | Bales et al. |
| 5,396,900 A | 3/1995 | Slater et al. | 5,669,883 A | 9/1997 | Scarfone et al. |
| 5,399,167 A | 3/1995 | Deniega | 5,672,161 A | 9/1997 | Allen |
| 5,403,283 A | 4/1995 | Luther | 5,679,907 A | 10/1997 | Ruck |
| 5,405,323 A | 4/1995 | Rogers et al. | 5,685,852 A | 11/1997 | Turkel et al. |
| 5,405,388 A | 4/1995 | Fox | 5,685,862 A | 11/1997 | Mahurkar |
| 5,409,461 A | 4/1995 | Steinman | 5,687,907 A | 11/1997 | Holden |
| 5,411,486 A | 5/1995 | Zadini | 5,690,619 A | 11/1997 | Erskine |
| 5,415,182 A | 5/1995 | Chin et al. | 5,693,022 A | 12/1997 | Haynes |
| 5,417,659 A | 5/1995 | Gaba | 5,693,031 A | 12/1997 | Ryan et al. |
| 5,417,709 A | 5/1995 | Slaterq | 5,695,467 A | 12/1997 | Miyata et al. |
| 5,419,766 A | 5/1995 | Chang et al. | 5,695,521 A | 12/1997 | Anderhub |
| 5,421,522 A | 6/1995 | Bowen | 5,697,904 A | 12/1997 | Raines et al. |
| 5,423,766 A | 6/1995 | Di Cesare | 5,697,907 A | 12/1997 | Gaba |
| 5,425,718 A | 6/1995 | Tay | 5,700,249 A | 12/1997 | Jenkins |
| 5,425,884 A | 6/1995 | Botz | 5,700,250 A | 12/1997 | Erskine |
| 5,429,138 A | 7/1995 | Jamshidi | 5,702,080 A | 12/1997 | Whittier et al. |
| 5,429,616 A | 7/1995 | Schaffer | 5,702,369 A | 12/1997 | Mercereau |
| 5,454,378 A | 10/1995 | Palmer et al. | 5,706,824 A | 1/1998 | Whitlier |
| 5,456,267 A | 10/1995 | Stark | 5,707,392 A | 1/1998 | Kortenbach |
| 5,458,658 A | 10/1995 | Sircom | 5,713,368 A | 2/1998 | Leigh |
| 5,462,062 A | 10/1995 | Rubinstein et al. | 5,713,888 A | 2/1998 | Neuenfeldt et al. |
| 5,466,223 A | 11/1995 | Bressler et al. | 5,715,832 A | 2/1998 | Kobhsh et al. |
| 5,471,992 A | 12/1995 | Banik et al. | 5,718,688 A | 2/1998 | Wozencroft |
| 5,473,629 A | 12/1995 | Muramolo | 5,722,422 A | 3/1998 | Palmer et al. |
| 5,476,099 A | 12/1995 | Robinson et al. | 5,730,150 A | 3/1998 | Peppel et al. |
| 5,476,102 A | 12/1995 | Como et al. | 5,730,724 A | 3/1998 | Plishka et al. |
| 5,478,313 A | 12/1995 | White | 5,735,827 A | 4/1998 | Adwers |
| 5,480,385 A | 1/1996 | Thome et al. | 5,738,660 A | 4/1998 | Luther |
| 5,482,054 A | 1/1996 | Slater et al. | 5,738,665 A | 4/1998 | Caizza |
| 5,487,734 A | 1/1996 | Thome et al. | 5,746,753 A | 5/1998 | Sullivan et al. |
| 5,492,532 A | 2/1996 | Ryan et al. | 5,752,923 A | 5/1998 | Terwilliger |
| 5,501,675 A | 3/1996 | Erskme | D395,609 S | 6/1998 | Knienem et al. |
| 5,507,296 A | 4/1996 | Bales et al. | 5,758,655 A | 6/1998 | Como Rodriguez et al. |
| 5,507,297 A | 4/1996 | Slater et al. | 5,776,157 A | 7/1998 | Thome et al. |
| 5,507,298 A | 4/1996 | Schramm et al. | 5,795,336 A | 8/1998 | Romano et al. |
| 5,514,100 A | 5/1996 | Mahurkar | 5,807,275 A | 9/1998 | Jamshidi |
| 5,514,152 A | 5/1996 | Smith | 5,807,277 A | 9/1998 | Swaim |
| 5,522,398 A | 6/1996 | Goldenberg et al. | 5,810,744 A | 9/1998 | Chu et al. |
| 5,526,821 A | 6/1996 | Jamshidi | 5,817,069 A | 10/1998 | Amett |
| 5,533,516 A | 7/1996 | Sahatjian | 5,823,970 A | 10/1998 | Terwilliger |
| 5,533,974 A | 7/1996 | Gaba | 5,823,971 A | 10/1998 | Robinson et al. |
| 5,538,009 A | 7/1996 | Byrne et al. | 5,823,997 A | 10/1998 | Thorne |
| 5,542,927 A | 8/1996 | Thome et al. | 5,824,002 A | 10/1998 | Gentelia et al. |
| 5,549,565 A | 8/1996 | Ryan et al. | D400,806 S | 11/1998 | Tillack |
| 5,549,708 A | 8/1996 | Thome et al. | D400,808 S | 11/1998 | Schwan |
| 5,553,624 A | 9/1996 | Francese et al. | 5,836,917 A | 11/1998 | Thome et al. |
| 5,558,651 A | 9/1996 | Crawford et al. | 5,836,920 A * | 11/1998 | Robertson ............ 604/192 |
| 5,562,629 A | 10/1996 | Haughton | 5,836,921 A | 11/1998 | Mahurkar |
| 5,562,633 A | 10/1996 | Wozencrofl | 5,840,044 A | 11/1998 | Dassa et al. |
| 5,562,683 A | 10/1996 | Chan | 5,843,001 A | 12/1998 | Goldenberg |

| Patent | Date | Inventor |
|---|---|---|
| 5,848,692 A | 12/1998 | Thome et al. |
| 5,853,393 A | 12/1998 | Bogert |
| 5,860,955 A | 1/1999 | Wright et al. |
| 5,865,806 A | 2/1999 | Howell |
| 5,871,453 A | 2/1999 | Banik et al. |
| 5,873,886 A | 2/1999 | Larsen et al. |
| 5,879,332 A | 3/1999 | Schwemberger et al. |
| 5,879,337 A | 3/1999 | Kuracina et al. |
| 5,879,338 A | 3/1999 | Mahurkar |
| 5,882,337 A | 3/1999 | Bogert et al. |
| 5,885,226 A | 3/1999 | Rubinstein et al. |
| 5,891,105 A | 4/1999 | Mahurkar |
| 5,893,845 A | 4/1999 | Newby |
| 5,893,876 A | 4/1999 | Turkel et al. |
| 5,895,361 A | 4/1999 | Turturro |
| 5,897,507 A | 4/1999 | Kortenbach et al. |
| 5,906,594 A | 5/1999 | Scarfone et al. |
| 5,910,130 A | 6/1999 | Caizza et al. |
| 5,910,132 A | 6/1999 | Schultz |
| 5,911,705 A | 6/1999 | Howell |
| 5,913,859 A | 6/1999 | Shapira |
| 5,916,175 A | 6/1999 | Bauer |
| 5,928,162 A | 7/1999 | Giutlino et al. |
| 5,928,163 A | 7/1999 | Roberts et al. |
| 5,928,200 A | 7/1999 | Thome et al. |
| 5,935,109 A | 8/1999 | Donnan |
| 5,947,930 A | 9/1999 | Schwemberger et al. |
| 5,951,489 A | 9/1999 | Bauer |
| 5,951,525 A | 9/1999 | Thome et al. |
| 5,951,582 A | 9/1999 | Thome et al. |
| 5,954,696 A | 9/1999 | Ryan |
| 5,954,698 A | 9/1999 | Pike |
| 5,957,863 A | 9/1999 | Koblish et al. |
| 5,957,887 A | 9/1999 | Osterlind et al. |
| 5,957,892 A | 9/1999 | Thorne |
| 5,961,526 A | 10/1999 | Chu et al. |
| 5,961,534 A | 10/1999 | Banik et al. |
| 5,964,717 A | 10/1999 | Gottlieb et al. |
| 5,967,490 A | 10/1999 | Pike |
| 5,976,115 A | 11/1999 | Parris et al. |
| 5,979,840 A | 11/1999 | Hollister et al. |
| 5,980,488 A | 11/1999 | Thorne |
| 5,989,196 A | 11/1999 | Chu et al. |
| 5,989,229 A | 11/1999 | Chiappetta |
| 5,989,241 A | 11/1999 | Pllshka et al. |
| 5,993,426 A | 11/1999 | Hollister |
| 6,000,846 A | 12/1999 | Gregory et al. |
| 6,001,080 A | 12/1999 | Kuracina et al. |
| 6,004,294 A | 12/1999 | Bnmhall et al. |
| 6,007,560 A | 12/1999 | Gottlieb et al. |
| 6,015,391 A | 1/2000 | Rishton et al. |
| 6,022,324 A | 2/2000 | Skinner |
| 6,024,708 A | 2/2000 | Bales et al. |
| 6,024,727 A | 2/2000 | Thome et al. |
| 6,033,369 A | 3/2000 | Goldenberg |
| 6,036,361 A | 3/2000 | Gregory et al. |
| 6,036,675 A | 3/2000 | Thome et al. |
| 6,047,729 A | 4/2000 | Hollister et al. |
| 6,050,954 A | 4/2000 | Mittermeier |
| 6,050,976 A | 4/2000 | Thome et al. |
| 6,053,877 A | 4/2000 | Banik et al. |
| 6,063,037 A | 5/2000 | Mittermeier et al. |
| 6,063,040 A | 5/2000 | Owen et al. |
| 6,071,284 A | 6/2000 | Fox |
| 6,080,115 A | 6/2000 | Rubinstein |
| 6,083,176 A | 7/2000 | Terwilliger |
| 6,083,202 A | 7/2000 | Smith |
| 6,086,563 A | 7/2000 | Moulton et al. |
| 6,090,078 A | 7/2000 | Erskine |
| 6,090,108 A | 7/2000 | McBrayer et al. |
| 6,095,967 A | 8/2000 | Black et al. |
| 6,096,005 A | 8/2000 | Botich |
| 6,102,920 A | 8/2000 | Sullivan et al. |
| 6,106,484 A | 8/2000 | Terwilliger |
| 6,110,128 A | 8/2000 | Andelin et al. |
| 6,110,129 A | 8/2000 | Terwilliger |
| 6,110,176 A | 8/2000 | Shapira |
| RE36,885 E | 9/2000 | Blecher et al. |
| 6,117,108 A | 9/2000 | Woehr et al. |
| 6,117,112 A | 9/2000 | Mahurkar |
| 6,117,115 A | 9/2000 | Hill et al. |
| 6,132,401 A | 10/2000 | Van Der Meyden |
| 6,135,110 A | 10/2000 | Roy |
| 6,142,956 A | 11/2000 | Kortenbach et al. |
| 6,142,957 A | 11/2000 | Diamond et al. |
| 6,149,629 A | 11/2000 | Wilson et al. |
| 6,171,284 B1 | 1/2001 | Kao |
| 6,174,292 B1 | 1/2001 | Kortenbach et al. |
| 6,193,671 B1 | 2/2001 | Turturro et al. |
| 6,197,007 B1 | 3/2001 | Thome et al. |
| 6,203,527 B1 | 3/2001 | Zadini |
| 6,210,373 B1 | 4/2001 | Allmon |
| 6,217,556 B1 | 4/2001 | Ellingson et al. |
| 6,221,029 B1 | 4/2001 | Mathie et al. |
| 6,221,047 B1 | 4/2001 | Greene et al. |
| 6,224,569 B1 | 5/2001 | Brimhall |
| 6,224,576 B1 | 5/2001 | Thome et al. |
| 6,234,773 B1 | 5/2001 | Hill et al. |
| 6,254,575 B1 | 7/2001 | Thome, Jr. et al. |
| 6,261,242 B1 | 7/2001 | Roberts et al. |
| 6,264,617 B1 | 7/2001 | Bales et al. |
| 6,280,399 B1 | 8/2001 | Rossin et al. |
| 6,280,401 B1 | 8/2001 | Mahurkar |
| 6,280,419 B1 | 8/2001 | Vojlasek |
| 6,280,420 B1 | 8/2001 | Ferguson et al. |
| D448,314 S | 9/2001 | Chen |
| 6,283,925 B1 | 9/2001 | Terwilliger |
| 6,287,278 B1 | 9/2001 | Woehr et al. |
| 6,302,852 B1 | 10/2001 | Fleming, III et al. |
| 6,309,376 B1 | 10/2001 | Alesi |
| 6,312,394 B1 | 11/2001 | Fleming, III |
| 6,315,737 B1 | 11/2001 | Skinner |
| 6,321,782 B1 | 11/2001 | Hollister |
| 6,322,537 B1 | 11/2001 | Chang |
| 6,328,701 B1 | 12/2001 | Terwilliger |
| 6,328,713 B1 | 12/2001 | Hollister |
| 6,334,857 B1 | 1/2002 | Hollister et al. |
| 6,336,915 B1 | 1/2002 | Scarfone et al. |
| 6,340,351 B1 | 1/2002 | Goldenberg |
| 6,358,252 B1 | 3/2002 | Shapira |
| 6,358,265 B1 | 3/2002 | Thome, Jr. et al. |
| 6,361,525 B2 | 3/2002 | Capes et al. |
| 6,379,333 B1 | 4/2002 | Brimhall et al. |
| 6,379,338 B1 | 4/2002 | Garvin |
| 6,383,144 B1 | 5/2002 | Mooney |
| 6,406,459 B1 | 6/2002 | Allman |
| 6,409,701 B1 | 6/2002 | Cohn et al. |
| 6,416,484 B1 | 7/2002 | Miller et al. |
| 6,423,034 B2 | 7/2002 | Scarfone et al. |
| 6,439,768 B1 | 8/2002 | Wu et al. |
| 6,443,910 B1 | 9/2002 | Krueger et al. |
| 6,443,927 B1 | 9/2002 | Cook |
| 6,443,929 B1 | 9/2002 | Kuracina et al. |
| 6,478,751 B1 | 11/2002 | Krueger et al. |
| 6,485,468 B2 | 11/2002 | Vojtasek |
| 6,485,473 B1 | 11/2002 | Lynn |
| 6,488,663 B1 | 12/2002 | Steg |
| 6,500,129 B1 | 12/2002 | Mahurkar |
| 6,501,384 B2 | 12/2002 | Chapman |
| 6,517,516 B1 | 2/2003 | Caizza |
| 6,519,569 B1 | 2/2003 | White et al. |
| 6,520,938 B1 | 2/2003 | Funderburk |
| 6,537,255 B1 | 3/2003 | Raines |
| 6,537,259 B1 | 3/2003 | Niemnann |
| 6,544,194 B1 | 4/2003 | Kortenbach et al. |
| 6,551,287 B1 | 4/2003 | Hollister |
| 6,551,328 B2 | 4/2003 | Kortenbach |
| 6,554,778 B1 | 4/2003 | Fleming, III |
| 6,569,125 B2 | 5/2003 | Jepson et al. |
| 6,575,919 B1 | 6/2003 | Feiley et al. |
| 6,582,402 B1 | 6/2003 | Erskine |
| 6,582,446 B1 | 6/2003 | Marchosky |
| 6,585,704 B2 | 7/2003 | Luther et al. |
| 6,592,556 B1 | 7/2003 | Thome |
| 6,595,954 B1 | 7/2003 | Luther |
| 6,595,955 B2 | 7/2003 | Ferguson et al. |
| 6,613,018 B2 | 9/2003 | Bagga et al. |
| 6,616,604 B1 | 9/2003 | Bass et al. |

| Patent No. | Date | Name |
|---|---|---|
| 6,616,630 B1 | 9/2003 | Woehr et al. |
| 6,623,458 B2 | 9/2003 | Woehr et al. |
| 6,626,850 B1 | 9/2003 | Chau et al. |
| D480,977 S | 10/2003 | Wawro et al. |
| D481,321 S | 10/2003 | Kmeriem et al. |
| 6,629,959 B2 | 10/2003 | Kuracina et al. |
| 6,634,789 B2 | 10/2003 | Babkes |
| 6,635,033 B1 | 10/2003 | Hill et al. |
| 6,638,252 B2 | 10/2003 | Moulton |
| 6,638,254 B2 | 10/2003 | Nakagami |
| 6,641,562 B1 | 11/2003 | Peterson |
| 6,652,486 B2 | 11/2003 | Bialecki et al. |
| 6,652,490 B2 | 11/2003 | Howell |
| 6,663,592 B2 | 12/2003 | Rhad et al. |
| 6,673,047 B2 | 1/2004 | Crawford |
| 6,673,060 B1 | 1/2004 | Fleming, III |
| 6,682,510 B2 | 1/2004 | Niermann |
| 6,689,102 B2 | 2/2004 | Greene |
| 6,692,471 B2 | 2/2004 | Boudreaux |
| 6,695,814 B2 | 2/2004 | Greene et al. |
| 6,698,921 B2 | 3/2004 | Siefert |
| 6,699,221 B2 | 3/2004 | Vaillancourt |
| 6,702,786 B2 | 3/2004 | Olovson |
| 6,709,419 B2 | 3/2004 | Woehr |
| 6,719,732 B2 | 4/2004 | Courteix |
| 6,723,075 B2 | 4/2004 | Davey et al. |
| 6,727,805 B2 | 4/2004 | Hollister et al. |
| 6,730,043 B2 | 5/2004 | Krueger et al. |
| 6,731,216 B2 | 5/2004 | Ho et al. |
| 6,740,063 B2 | 5/2004 | Lynn |
| 6,749,576 B2 | 6/2004 | Bauer |
| 6,749,588 B1 | 6/2004 | Howell et al. |
| 6,749,595 B1 | 6/2004 | Murphy |
| 6,755,793 B2 | 6/2004 | Lamoureux et al. |
| 6,761,704 B2 | 7/2004 | Crawford |
| 6,761,706 B2 | 7/2004 | Vaillancourt |
| 6,764,567 B2 | 7/2004 | Sperko et al. |
| 6,767,336 B1 | 7/2004 | Kaplan |
| 6,770,050 B2 | 8/2004 | Epstein |
| 6,770,053 B2 | 8/2004 | Scarfone et al. |
| 6,796,962 B2 | 9/2004 | Ferguson et al. |
| 6,798,348 B1 | 9/2004 | Wilker et al. |
| 6,811,308 B2 | 11/2004 | Chapman |
| 6,821,267 B2 | 11/2004 | Veillon, Jr. et al. |
| 6,827,488 B2 | 12/2004 | Knienem et al. |
| 6,832,990 B2 | 12/2004 | Kortenbach et al. |
| 6,832,992 B2 | 12/2004 | Wilkinson |
| 6,839,651 B2 | 1/2005 | Lantz et al. |
| 6,846,314 B2 | 1/2005 | Shapira |
| 6,849,051 B2 | 2/2005 | Sramek et al. |
| 6,855,128 B2 | 2/2005 | Swenson |
| 6,855,130 B2 | 2/2005 | Saulenas et al. |
| 6,860,871 B2 | 3/2005 | Kuracina et al. |
| 6,875,183 B2 | 4/2005 | Cervi |
| 6,890,308 B2 | 5/2005 | Islam |
| 6,902,546 B2 | 6/2005 | Ferguson |
| 6,916,292 B2 | 7/2005 | Morawski et al. |
| 6,916,311 B2 | 7/2005 | Vojtasek |
| 6,916,314 B2 | 7/2005 | Schneider |
| 6,923,813 B2 | 8/2005 | Phillips et al. |
| 6,936,036 B2 | 8/2005 | Wilkinson |
| D512,506 S | 12/2005 | Layne et al. |
| D512,924 S | 12/2005 | Ikeda |
| 6,976,783 B2 | 12/2005 | Chen |
| 6,981,948 B2 | 1/2006 | Pellegrmo et al. |
| 6,984,213 B2 | 1/2006 | Homer et al. |
| 6,989,003 B2 | 1/2006 | Wing et al. |
| 7,008,402 B2 | 3/2006 | Ferguson et al. |
| 7,018,343 B2 | 3/2006 | Plishka |
| 7,021,824 B2 | 4/2006 | Wawro et al. |
| 7,033,324 B2 | 4/2006 | Giusti et al. |
| 7,036,984 B2 | 5/2006 | Penney et al. |
| 7,063,703 B2 | 6/2006 | Reo |
| 7,112,191 B2 | 9/2006 | Daga |
| 7,118,552 B2 | 10/2006 | Shaw |
| 7,207,973 B2 | 4/2007 | Barrelle |
| 7,214,208 B2 | 5/2007 | Vaillancourt |
| 7,226,434 B2 | 6/2007 | Carlyon et al. |
| 7,238,169 B2 | 7/2007 | Takagi et al. |
| 7,247,148 B2 | 7/2007 | Murashila |
| 7,255,475 B2 | 8/2007 | Quinn et al. |
| 7,264,613 B2 | 9/2007 | Woehr et al. |
| 7,300,420 B2 | 11/2007 | Doyle |
| 7,303,548 B2 | 12/2007 | Rhad et al. |
| 7,316,507 B2 | 1/2008 | Sisk et al. |
| 7,357,784 B2 | 4/2008 | Ferguson |
| 7,377,908 B2 | 5/2008 | Buelikofer et al. |
| 7,488,306 B2 | 2/2009 | Nguyen |
| 7,500,965 B2 | 3/2009 | Menzi et al. |
| 7,513,888 B2 | 4/2009 | Sircom |
| 2001/0021827 A1 | 9/2001 | Ferguson et al. |
| 2002/0021827 A1 | 2/2002 | Smith |
| 2002/0032421 A1* | 3/2002 | Scott et al. ............ 604/367 |
| 2003/0002562 A1 | 1/2003 | Yerlikaya et al. |
| 2003/0100868 A1 | 5/2003 | Ferguson et al. |
| 2003/0114797 A1 | 6/2003 | Vaillancourt et al. |
| 2003/0144627 A1 | 7/2003 | Woehr et al. |
| 2003/0176810 A1 | 9/2003 | Maahs et al. |
| 2003/0191438 A1 | 10/2003 | Ferguson et al. |
| 2003/0220617 A1 | 11/2003 | Dickerson |
| 2004/0071182 A1 | 4/2004 | Quinn et al. |
| 2004/0077973 A1 | 4/2004 | Groenke et al. |
| 2004/0078003 A1 | 4/2004 | Smith et al. |
| 2004/0078007 A1 | 4/2004 | Nguyen |
| 2004/0092889 A1 | 5/2004 | Ferguson et al. |
| 2004/0133167 A1 | 7/2004 | Ferguson et al. |
| 2004/0153005 A1 | 8/2004 | Krueger |
| 2004/0171989 A1 | 9/2004 | Homer et al. |
| 2004/0186434 A1 | 9/2004 | Harding et al. |
| 2004/0225260 A1 | 11/2004 | Villa et al. |
| 2004/0236288 A1 | 11/2004 | Howell et al. |
| 2004/0236289 A1 | 11/2004 | Ferguson et al. |
| 2005/0027263 A1 | 2/2005 | Woehr et al. |
| 2005/0043691 A1 | 2/2005 | Ferguson |
| 2005/0054987 A1 | 3/2005 | Perez et al. |
| 2005/0070850 A1 | 3/2005 | Albrecht |
| 2005/0070851 A1 | 3/2005 | Thompson et al. |
| 2005/0070855 A1 | 3/2005 | Ferguson et al. |
| 2005/0075609 A1 | 4/2005 | Latona |
| 2005/0090763 A1 | 4/2005 | Wang |
| 2005/0090764 A1 | 4/2005 | Wang |
| 2005/0113716 A1 | 5/2005 | Mueller, Jr. et al. |
| 2005/0119652 A1 | 6/2005 | Velter et al. |
| 2005/0131345 A1 | 6/2005 | Miller |
| 2005/0137500 A1 | 6/2005 | Wingler |
| 2005/0165404 A1 | 7/2005 | Miller |
| 2005/0192536 A1 | 9/2005 | Takagi et al. |
| 2005/0203459 A1 | 9/2005 | Alchas |
| 2005/0267383 A1 | 12/2005 | Groenke et al. |
| 2005/0273057 A1 | 12/2005 | Popov |
| 2005/0277845 A1 | 12/2005 | Cooke et al. |
| 2005/0288605 A1 | 12/2005 | Pellegrino et al. |
| 2006/0052721 A1 | 3/2006 | Dunker et al. |
| 2006/0064101 A1 | 3/2006 | Arramon |
| 2006/0116603 A1 | 6/2006 | Shibazaki et al. |
| 2006/0178625 A1 | 8/2006 | Lim et al. |
| 2006/0189934 A1 | 8/2006 | Kuracina et al. |
| 2006/0189936 A1 | 8/2006 | Carlyon et al. |
| 2006/0200195 A1 | 9/2006 | Yang |
| 2006/0276772 A1 | 12/2006 | Moos et al. |
| 2007/0110122 A1 | 5/2007 | Sisk et al. |
| 2007/0116089 A1 | 5/2007 | Bisch et al. |
| 2008/0097345 A1 | 4/2008 | Ferguson |
| 2008/0112461 A1 | 5/2008 | Bisch et al. |
| 2008/0294065 A1 | 11/2008 | Waldhoff et al. |

FOREIGN PATENT DOCUMENTS

| | | |
|---|---|---|
| JP | 6-241914 | 9/1994 |
| WO | WO 97-42989 | 11/1997 |
| WO | WO 2004/060138 | 7/2004 |
| WO | WO 2004/091687 | 10/2004 |
| WO | WO 2005/009246 | 2/2005 |
| WO | WO 2005/053774 | 6/2005 |
| WO | WO 2005/060679 | 7/2005 |

* cited by examiner

DEVICE FOR SHIELDING A SHARP TIP OF A CANNULA AND METHOD OF USING THE SAME

RELATED APPLICATIONS

This application is a divisional application under 35 U.S.C. 121 and claims the benefit to pending U.S. application Ser. No. 11/179,143 filed Jul. 11, 2005, entitled DEVICE FOR SHIELDING A SHARP TIP OF A CANNULA AND METHOD OF USING THE SAME, which is incorporated by reference in its entirety for all purposes.

BACKGROUND OF THE INVENTION

The present invention relates generally to a safety device, and more particularly to a device for shielding a sharp tip of a tubular needle.

Needle assemblies have particular, although not exclusive application in the field of medicine and have tubular needles with sharpened ends for use in piercing the skin to withdraw materials as needed. The needle is supported by some other structure that is used to manipulate the needle. The most common example is a syringe. However, some needle assemblies require the application of substantial force in use. One example of such a needle assembly is a bone marrow needle assembly that is used to penetrate cortical bone to reach the intramedullary canal for withdrawing liquid or a biopsy sample of bore marrow, or for infusing the canal with a selected material. Typically, the needle includes a cannula and a stylet that is received in the cannula and has a hard, sharp tip that can penetrate cortical bone. The tip projects out from the distal end of the cannula. The stylet can be withdrawn from the cannula after the needle penetrates the bone so that the hollow interior of the cannula can be used as a conduit for liquid or a receptacle to collect bone marrow.

In order to penetrate cortical bone, a substantial amount of force must be applied to the needle. For this reason, bone needle assemblies conventionally mount the needle in a handle that is sized and shaped so that the technician may comfortably grip the handle and apply the force necessary to penetrate the bone. The handle may comprise two handle members that can be selectively put together and separated for inserting the stylet into the cannula and removing the stylet from the cannula. A proximal handle member mounts the stylet and a distal handle member mounts the cannula. "Proximal" and "distal" refer to the relative location of the handle members to the technician when the needle assembly is in use. The proximal handle member is in contact with the palm of the technician's hand in use, and the distal handle member is on the opposite side of the proximal handle member from the palm.

Some needle assemblies, including bone needle assemblies, have associated safety mechanisms that shield the sharp tips of the needle components when they are not needed and after they have become contaminated with potentially hazardous biological material. The safety mechanism includes a shield and usually a mechanism for locking the shield in place over the sharpened tip. As a matter of convenience, and to enhance the probability that the safety feature will be used by a medical technician, the safety feature may be secured to the needle assembly. However, the safety feature must be retained out of the way when the needle assembly is being used, for example, to collect a liquid or solid sample from the intramedullary canal. The safety feature then must be released from its stowed position and moved to an operative position in which its shield covers the sharpened tip of the needle. While effective, this safety feature adds cost to the needle assembly and requires a conscious effort to use.

In cases where a sample (e.g., a bone marrow sample) is collected by the needle assembly, the sample has to be removed from the needle assembly. An obturator is a device including a long thin shaft that can fit inside the cannula for pushing the sample of bone marrow out of the cannula. This can be done with the safety shield in position covering the sharp end of the cannula to protect the technician. In some cases it will be determined that the sample is not satisfactory and it will be necessary to obtain a second sample. It is not necessary to use a new needle assembly, because the needle assembly would be reused on the same patient. However, the shield is held in place over the tip of the needle assembly making it unusable for a collecting a second sample. Accordingly, there is a need for a needle assembly that can be easily reset for second use, but which will not result in inadvertent release of the safety shield.

SUMMARY OF THE INVENTION

In general, the present invention relates to a safety device for shielding a sharp tip of a cannula having an interior passage including first and second opposite ends. The safety device includes a shaft sized and shaped for being received into the passage of the cannula through the first end of the passage and extending to the second end of the passage. A shield associated with the shaft is constructed for receiving and substantially shielding the sharp tip of the cannula upon reception of the shaft in the cannula passage. A catch associated with the shaft is adapted to prevent withdrawal of the shaft from the passage of the cannula when the shaft is received in the passage in a position where the shield receives the sharp tip of the cannula.

In another aspect, a needle assembly for use in collecting samples of tissues and/or bodily fluids generally includes a cannula at least partially defining an interior passage including first and second ends. The passage is adapted to receive the tissue and/or bodily fluid sample. A shaft is sized and shaped for being received into the passage of the cannula through the first end of the passage and extending to the second end of the passage for use in removing a sample collected in the cannula. A shield associated with the shaft is constructed for receiving and substantially shielding the sharp tip of the cannula upon reception of the shaft in the cannula passage. A catch associated with the shaft is adapted to engage the needle assembly to prevent withdrawal of the shaft from the passage of the cannula when the shaft is received in the passage in a position where the shield receives the sharp tip of the cannula.

In yet another aspect, a method of shielding a sharp tip of a cannula at least partially defining an interior passage including first and second opposite ends includes collecting a sample of tissue and/or bodily fluid from a patient in the passage of the cannula. A shaft is inserted into the passage through the first end thereof pushes the sample out of the second end of the passage to collect the sample. The step of inserting includes shielding the sharp tip of the cannula with a shield when the shaft is inserted a predetermined distance into the cannula. The shaft is retained relative to the cannula against movement out of the passage through the first end holds the shield over the sharp tip.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
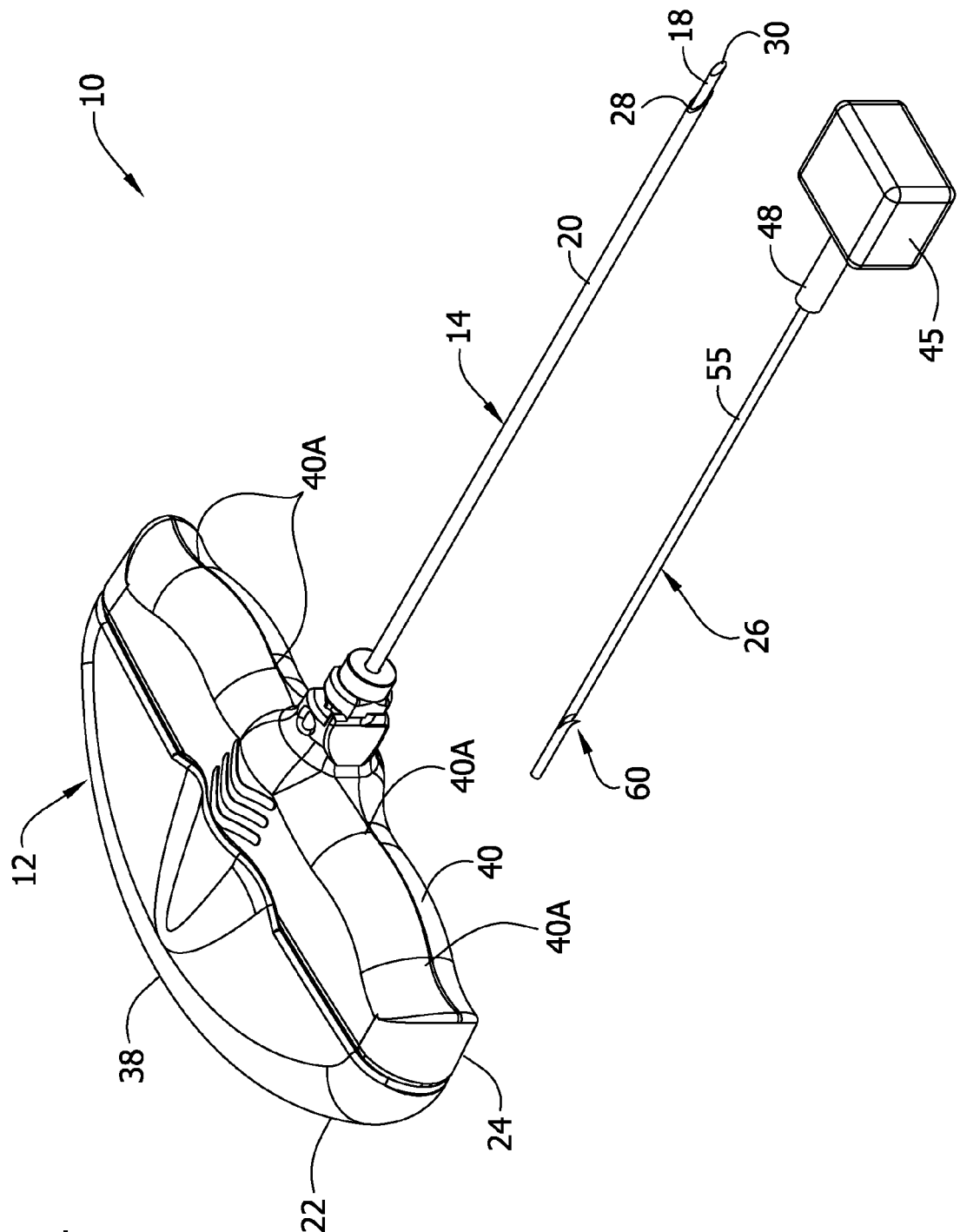
FIG. 1 is a perspective of a bone marrow needle assembly including a needle and an obturator of new construction.

Referring now to the drawings and in particular to FIG. 1, a medical instrument constructed according to the principles of the present invention is shown in the form of a bone needle assembly, generally indicated at 10. The bone needle assembly includes a handle 12 (broadly, "mounting structure") and a needle 14, all reference numbers indicating their subjects generally. The needle 14 includes a stylet 18 and a cannula 20 that can receive the stylet. The handle 12 includes a first or proximal handle member (indicated generally at 22) mounting the stylet 18, and a second or distal handle member (indicated generally at 24) mounting the cannula 20. It will be understood that a needle could include only a single component part, or more than two parts within the scope of the present invention. Similarly, a handle could be a single part or more than two parts. The mounting structure for the needle 14 can be other than a handle without departing from the present invention. The needle assembly 10 further includes a safety device in the form of a modified obturator, generally indicated at 26, constructed according to the teachings of the present invention. The modified obturator 26 may be used to shield a sharp tip 28 of the cannula 20, as described more fully below, and may be used to remove a sample captured in the cannula.

The cannula 20 has a central axial passage extending the length of the cannula and an opening at both ends of the cannula. The distal tip 28 of the cannula 20 is beveled and sharpened. A proximal end portion of the cannula 20 is received in the distal handle member 24, and the opening of the end portion extends through the handle. The stylet 18 is solid and includes a sharp distal tip 30, and a proximal end portion received in the proximal handle member 22. The stylet 18 can be inserted through the axial passage opening in the proximal end portion of the cannula 20. The stylet 18 can be received entirely through the axial passage of the cannula so that its sharp distal tip projects axially outward from the distal tip 28 of the cannula. The stylet 18 provides the tool for penetrating the cortical bone, and can be removed from the cannula 20 once the intramedullary canal is accessed by the needle 14. The stylet 18 and cannula 20 are preferably constructed from strong, generally rigid metal, although they may be constructed from other materials.

The handle 12 formed by the proximal and distal handle members 22, 24 has an ergonomic shape that can be comfortably received in a medical technician's hand, and allows the technician to easily control the needle assembly 10 as he or she applies the substantial forces needed to penetrate the bone. More specifically, the top or proximal surface 38 of the proximal handle member 22 is rounded in conformance with the shape of the palm of the hand. The bottom or distal surface 40 of the distal handle member 24 is also rounded, but is undulating in shape thereby forming finger wells 40A for receiving the technician's fingers. The form of the handle can be other than described herein without departing from the scope of the present invention. The proximal and distal handle members 22, 24 can be connected together in a suitable manner when the stylet 18 is received in the cannula 20 (as illustrated in FIG. 1), so that the handle 12 acts essentially as a single piece when used to drive the needle 14 through a patient's skin and into the bone. The proximal and distal handle members 22, 24 can be disconnected and moved apart for removing the stylet 18 from the cannula 20. The handle is preferably constructed of plastic material, although it may be constructed of other material.

The needle assembly 10 is driven into the bone by grasping the handle 12 and pushing the stylet 18 through the skin, underlying tissue and cortical bone. Once this penetration has been achieved, the stylet 18 is no longer required. The proximal handle member 22 is disconnected from the distal handle member 24 and moved axially away from the distal handle member so that the stylet 18 slides out of the central axial passage of the cannula 20 while the cannula remains in the bone. In order to collect a sample of bone marrow, the distal handle member is advanced further into the bone. The sharp tip 28 of the cannula 20 cuts into the bone marrow and a sample is received in the central axial passage of the cannula. The cannula 20 can then be withdrawn from the patient by pulling on the distal handle member 24. The sample should remain lodged in the central axial passage of the cannula 20 near the sharp tip 28. It will be understood that a needle assembly may be used to collect a sample other than of bone marrow within the scope of the present invention.

Figure 2:
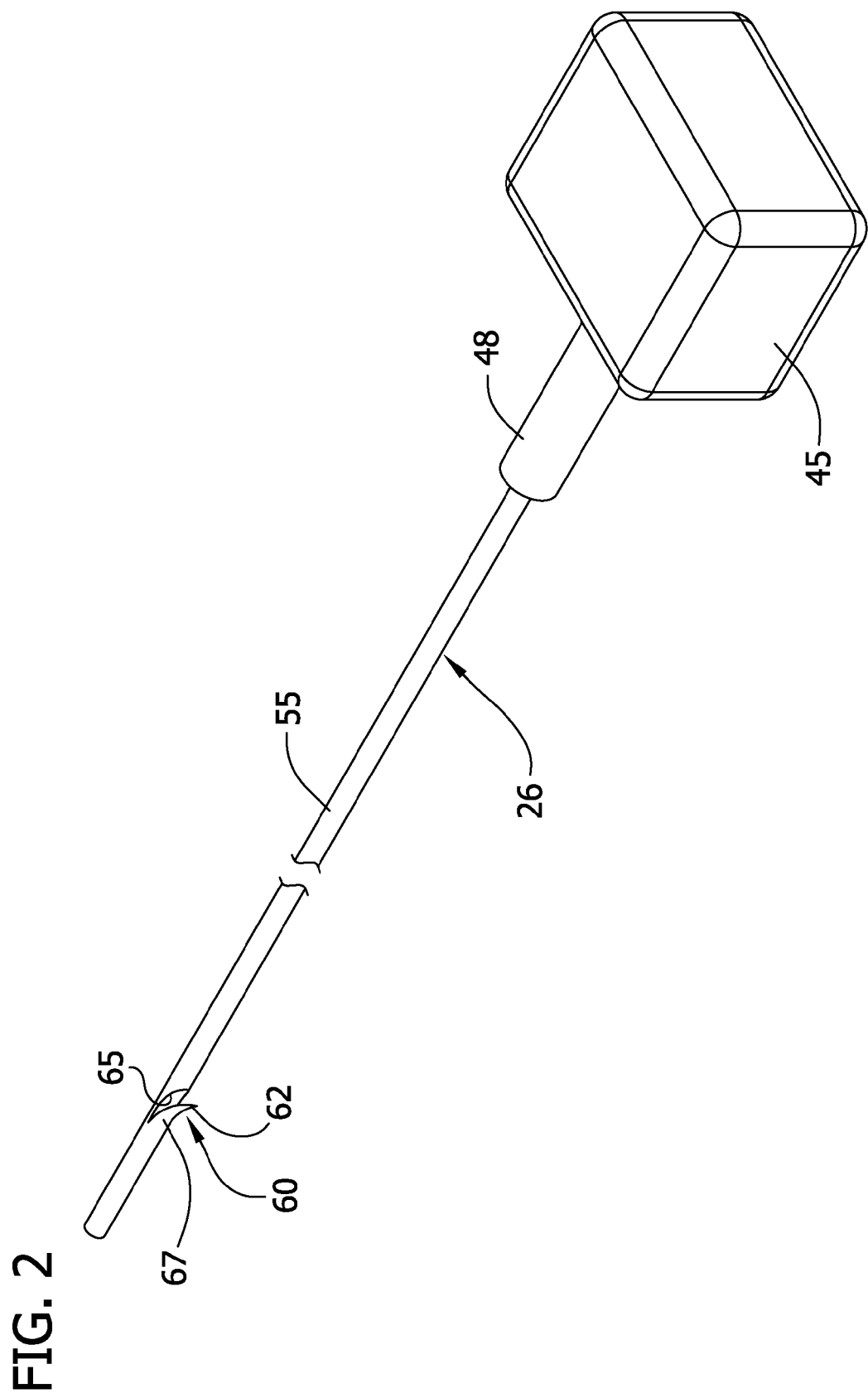
FIG. 2 is an enlarged fragmentary perspective of the obturator of FIG. 1.
Figure 3:
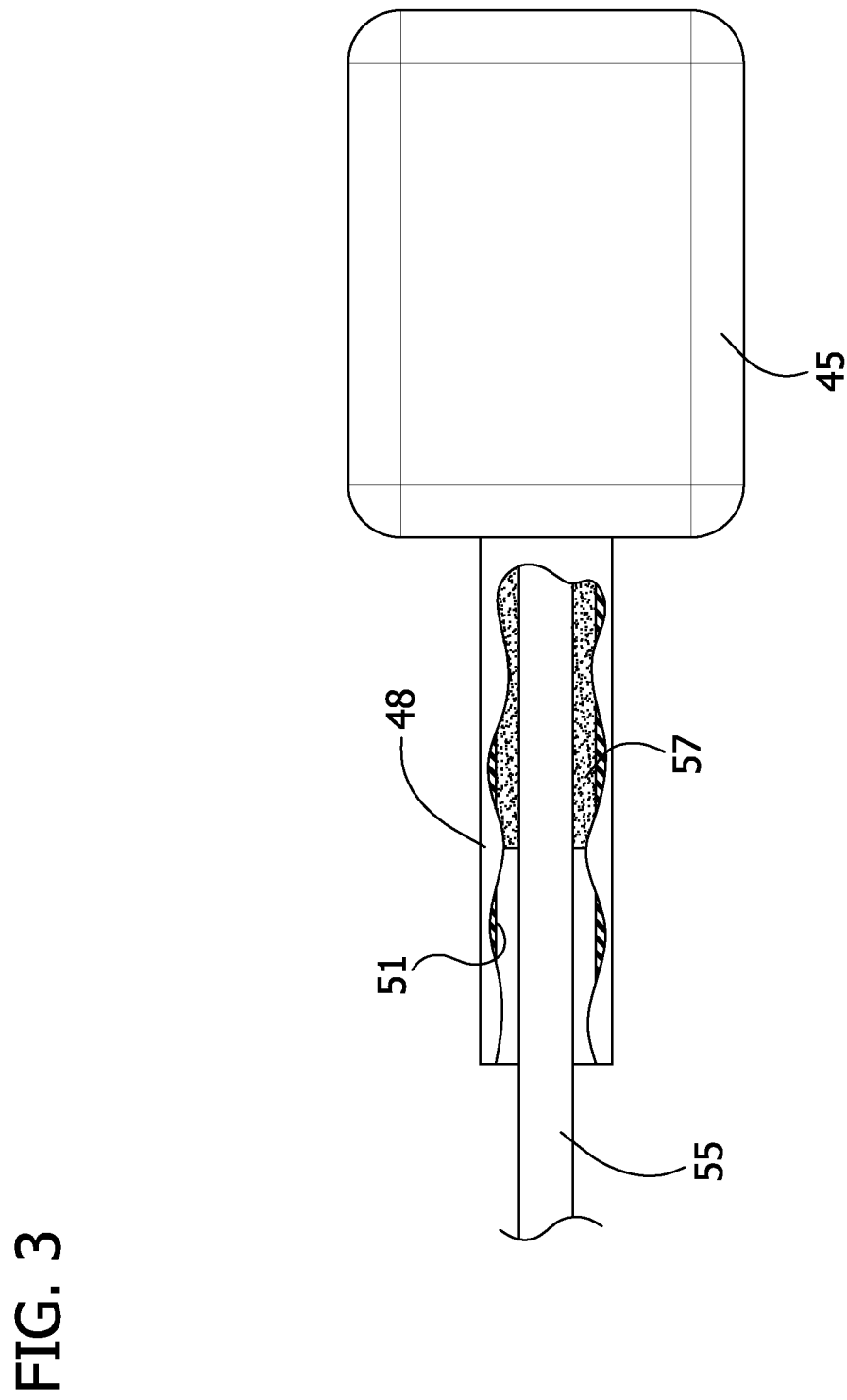
FIG. 3 is a further enlarged fragmentary side elevation of the obturator of FIG. 1 with a longitudinal portion of the a shield of the obturator broken away to reveal the interior.

Referring to FIGS. 2 and 3, the obturator 26 can be used to remove a lodged sample of bone marrow that has been collected in the central axial passage of cannula 20. The obturator 26 includes a grip 45 that is sized and shaped to be grasped by a user for manipulating the obturator 26, as will be described. A generally tubular shield 48 extends from the grip 45 and has a closed end associated with the grip, an opposite open end and an annular chamber 51 located generally between the ends. The grip 45 and the shield 48 are preferably integrally formed and constructed of a plastic material, although it is contemplated that the grip and shield may be formed separately and/or constructed of other material. As shown best in FIG. 8, a long, thin shaft 55 that is sized to be received in the central axial passage of the cannula 20 in a generally close fitting relation therein extends from the closed end of the tubular body of the shield 48 through the open end of the tubular body and is generally coaxial with the cylindrical chamber 51. The shaft 55 is preferably constructed of rigid metal material, although other types of material may be used.

The chamber 51 is sized and shaped for snugly receiving at least the sharp tip 28 of the cannula 20 of the needle 14 when the shaft 55 is received in the axial passage of the cannula. In the illustrated embodiment, a hematic absorbent body 57 is disposed within the chamber 51. The absorbent body 57 surrounds the shaft 55. The body 57 can be penetrated for receiving at least the tip 28 of the cannula 20 and is absorbent for absorbing biological fluids. In one embodiment, the absorbent body 57 can be made of an anti-microbial material to inhibit the growth of bacteria. The absorbent body 57 retains biological fluid, such as blood and other fluids that may flow out of the tip 28 of the cannula 20 within the shield 48. The body 57 may be constructed of a sponge material or plastic-type material or any other material that is generally known in the art for use in absorbing biological fluid, and in particular, such fluid flowing from a needle. The absorbent body 57 may be formed in other ways or omitted within the scope of the present invention.

Figure 4:
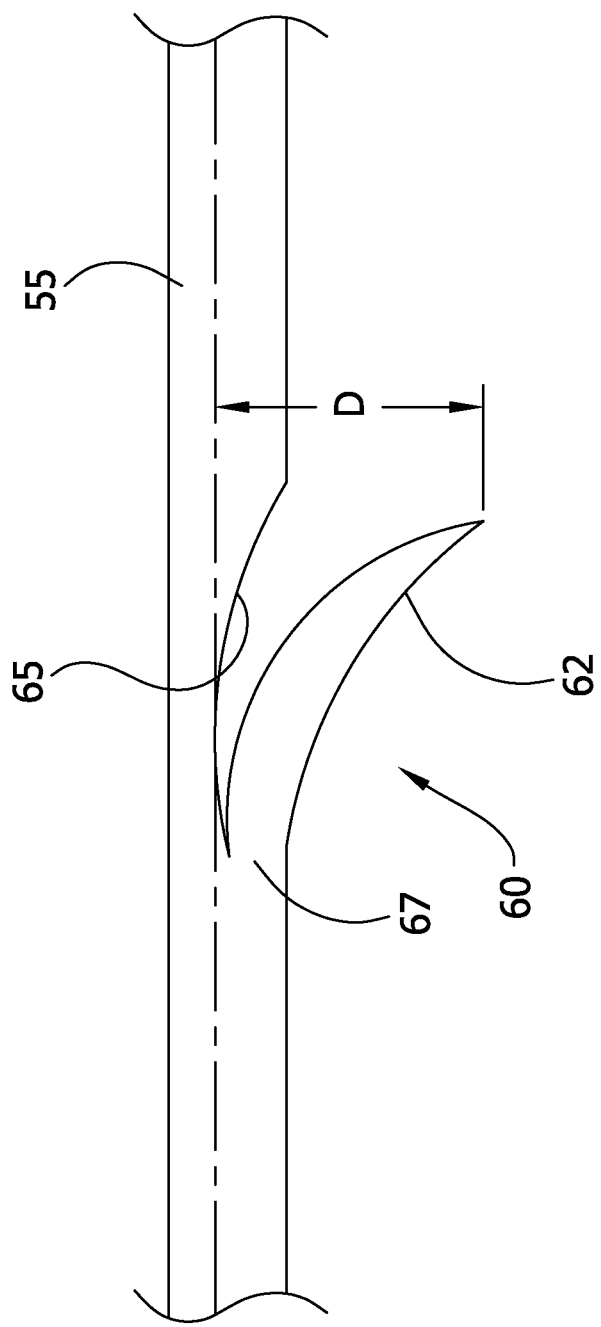
FIG. 4 is an enlarged fragmentary elevation of the obturator of FIG. 1 illustrating a catch on a shaft of the obturator in an extended position protruding laterally outward from the shaft.
Figure 5:
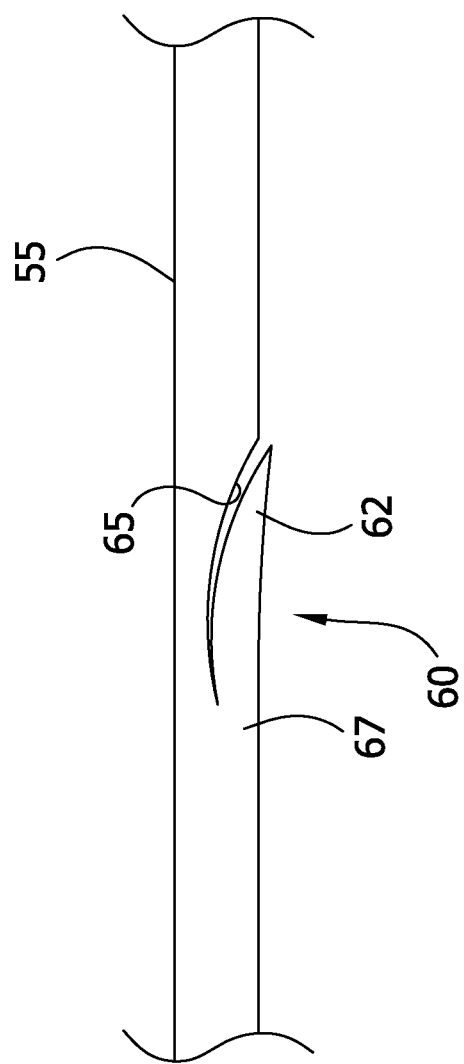
FIG. 5 is the enlarged fragmentary elevation of FIG. 4 but illustrating the catch in a retracted position.

Referring to FIGS. 2 and 4-5, a catch generally indicated at 60 is disposed on the shaft 55 of the obturator 26 generally adjacent the free end of the shaft. The catch 60 of the illustrated embodiment comprises a flap 62 connected to the shaft 55 so that the flap can pivot about an axis transverse to the shaft. The shaft 55 has a recess 65 sized and shaped to conformally receive the flap 62. The flap 62 and the associated recess 65 is formed by cutting out a longitudinal segment of the shaft 55 while leaving an end opposite the free end of the flap attached to the shaft to form a living hinge 67. The flap 62 is pivotable about the hinge 67 between an extended position (FIG. 4), in which the flap projects generally laterally outward from the shaft 55, and a retracted position (FIG. 5), in which the flap is substantially received in the recess 65. The exterior surface of the flap 62 and the exterior surface of the shaft 55 are generally flush when the flap is in the retracted position (FIG. 5). In the illustrated embodiment, only a small portion of the flap 62 remains attached to the shaft 55, and the flap is biased in the extended position. For reasons which will become apparent, the flap 62 is formed so that it is biased to pivot toward the free end of the shaft 55. Also, the hinge 67 should be strong enough to withstand at least some repetitious pivoting of the flap 62. As explained below, the length of the flap 62 and the angle at which the flap is biased to extend from shaft 55 is not crucial as long as the radial distance D (FIG. 4) between the free end of the flap and the central axis of the shaft is somewhat greater than the radius of the opening of the axial passage of the cannula 20 at the proximal end.

It is contemplated that the flap 62 may be formed separate from the shaft 55 and attached thereto in a suitable fashion (not illustrated). For example, a flap may be attached to a shaft 55 by welding or by other ways form the living hinge, or the flap may be attached using a hinge other than a living hinge. For example, a spring hinge can be used to bias the flap or a non-biasing hinge may be used along with other ways of properly biasing the flap, such as a spring associated with the free end portion of the flap. Also, it is contemplated that a shaft may not have a recess for receiving the flap. Instead, the flap can comprise a thin sheet, preferably of metal, having inner face for contacting the surface of the shaft and an outer face. Both faces have the same shape and generally the same radius of curvature as the surface of the shaft such that the flap lies generally flush against the surface of the shaft when it is in its retracted position. Other ways of forming and using a flap of the present invention are contemplated and within the scope of this invention.

Figure 6:
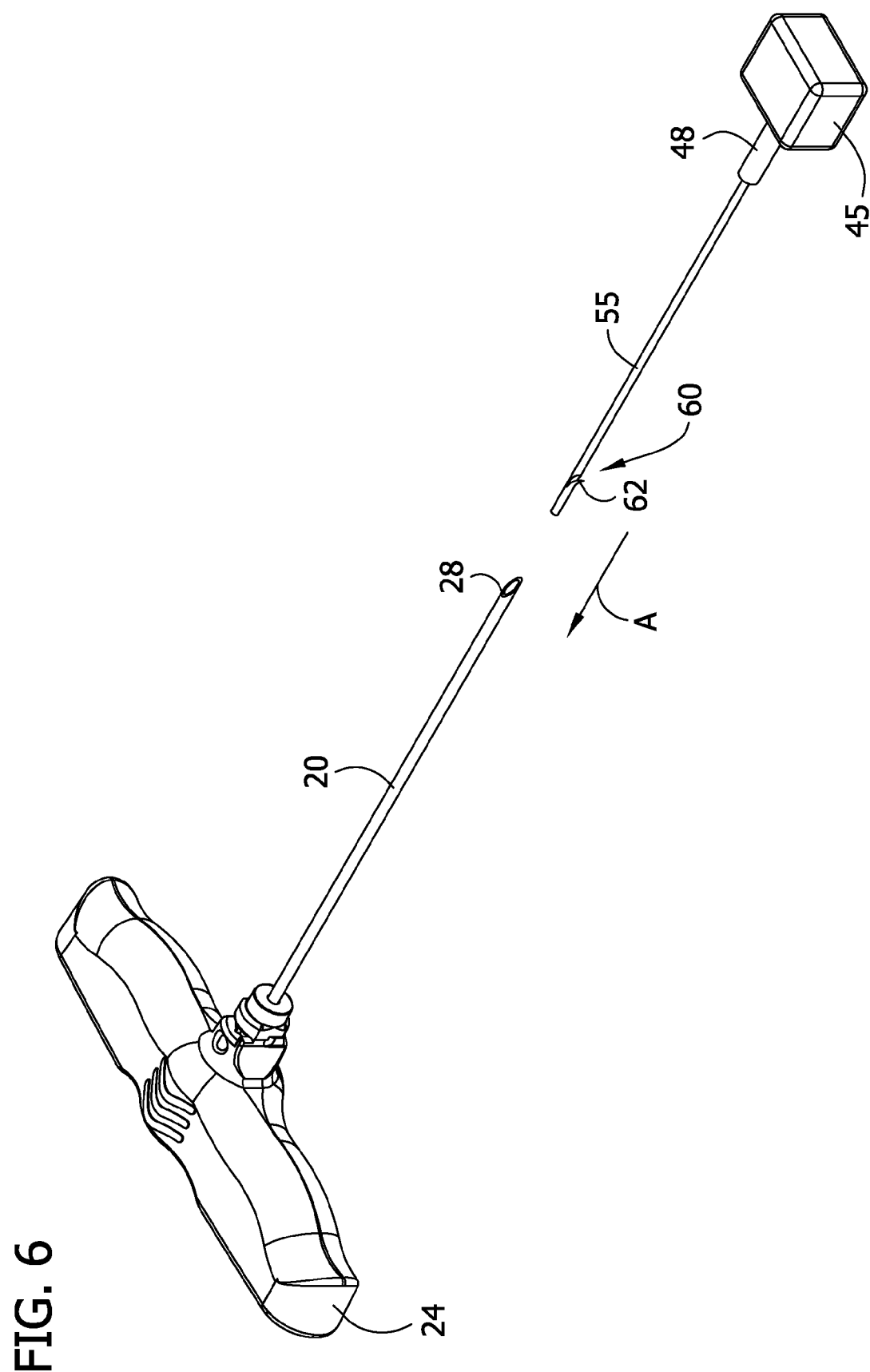
FIG. 6 is a perspective of the shaft of the obturator of FIG. 1 axially aligned with a passage of the needle of FIG. 1.
Figure 7:
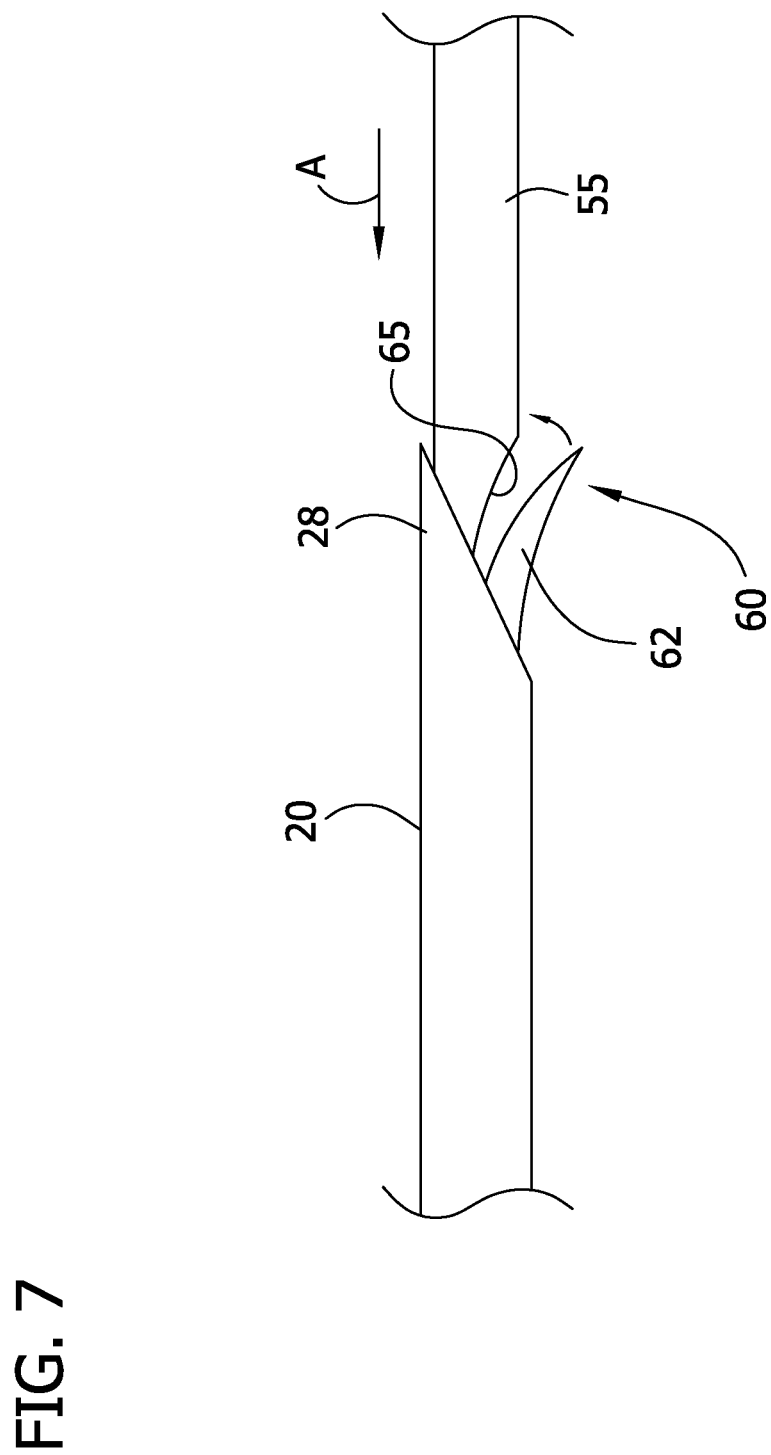
FIG. 7 is an enlarged fragmentary elevation of the needle and obturator of FIG. 6, but showing the shaft of the obturator received partially in the needle.

Referring to FIG. 6, the initial position of the obturator 26 with the free end of the shaft 55 aligned with the central axial passage of the cannula 20 at the tip 28 is shown. As explained above, the flap 62 is initially in the extended position (i.e., extending generally transversely from the shaft 55). As shown by directional arrow A in FIGS. 6 and 7, the grip 45 is pushed to advance the shaft 55 into the central axial passage, and as the shaft advances, the flap 62 contacts the tip 28 at its end including the living hinge 67, forcing the flap to pivot or fold down toward the recess 65. Eventually during the advancement of the shaft 55 within the cannula passage, the flap 62 is pushed by engagement with the cannula 20 to its retracted position whereby it is substantially received in the recess 65 and its outer surface is substantially flush with the outer surface of the shaft 55 of the obturator 26 (see e.g., FIG. 5). The flap 62 remains generally in the retracted position while inside the passage because of the generally tight fit between shaft 55 and the passage. The shaft 55 of the obturator 26 can continue to advance within the passage without significant impedance from the flap 62. As the shaft 55 advances, it pushes the sample toward the opening at proximal end of the central axial passage and out of the cannula where it can be collected in a Petri dish or other suitable container.

Figure 8:
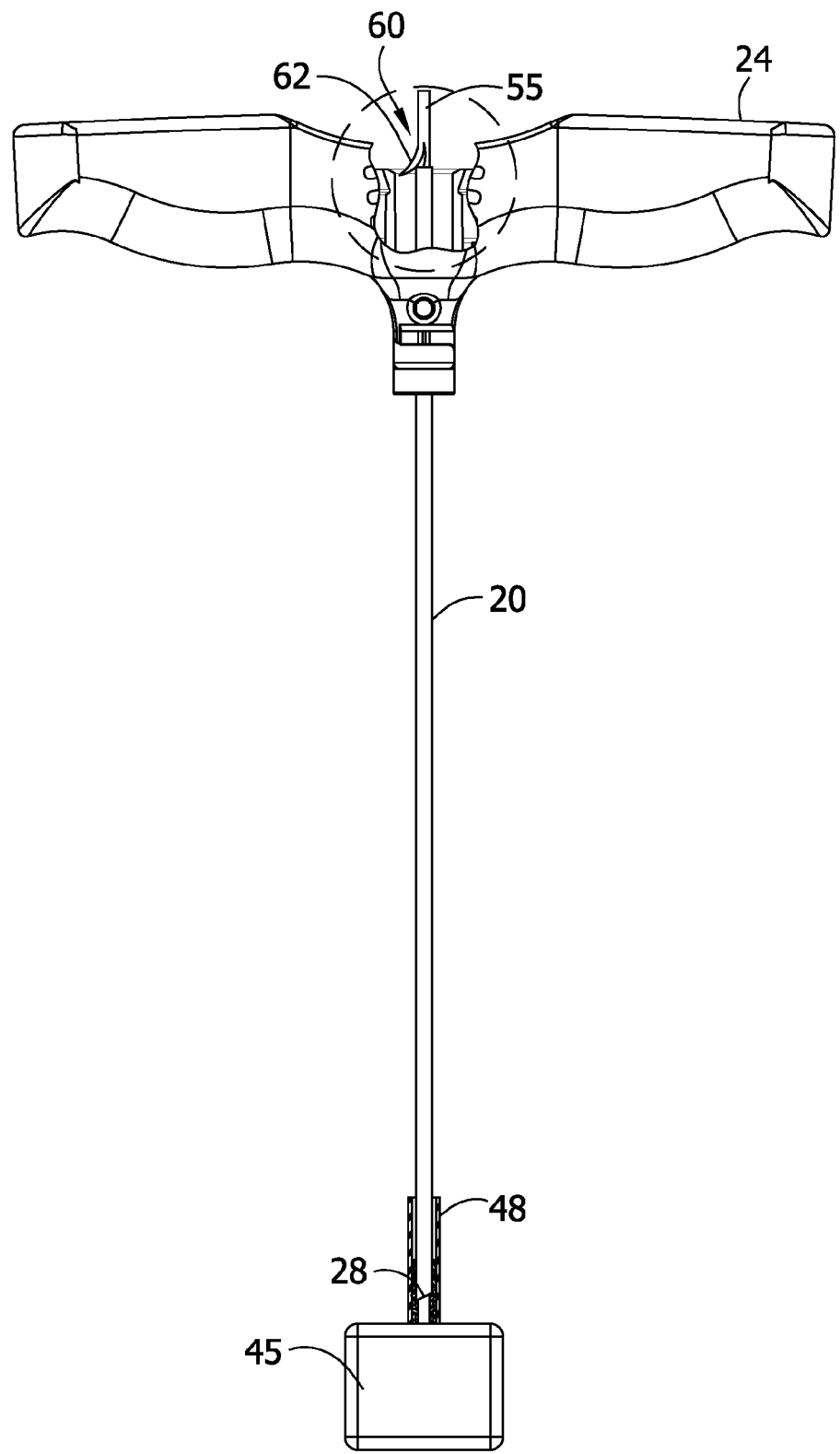
FIG. 8 is a side elevation of a distal handle member and cannula of the needle assembly with the obturator fully inserted into the needle and parts of the needle shield broken away to show internal components.
Figure 9:
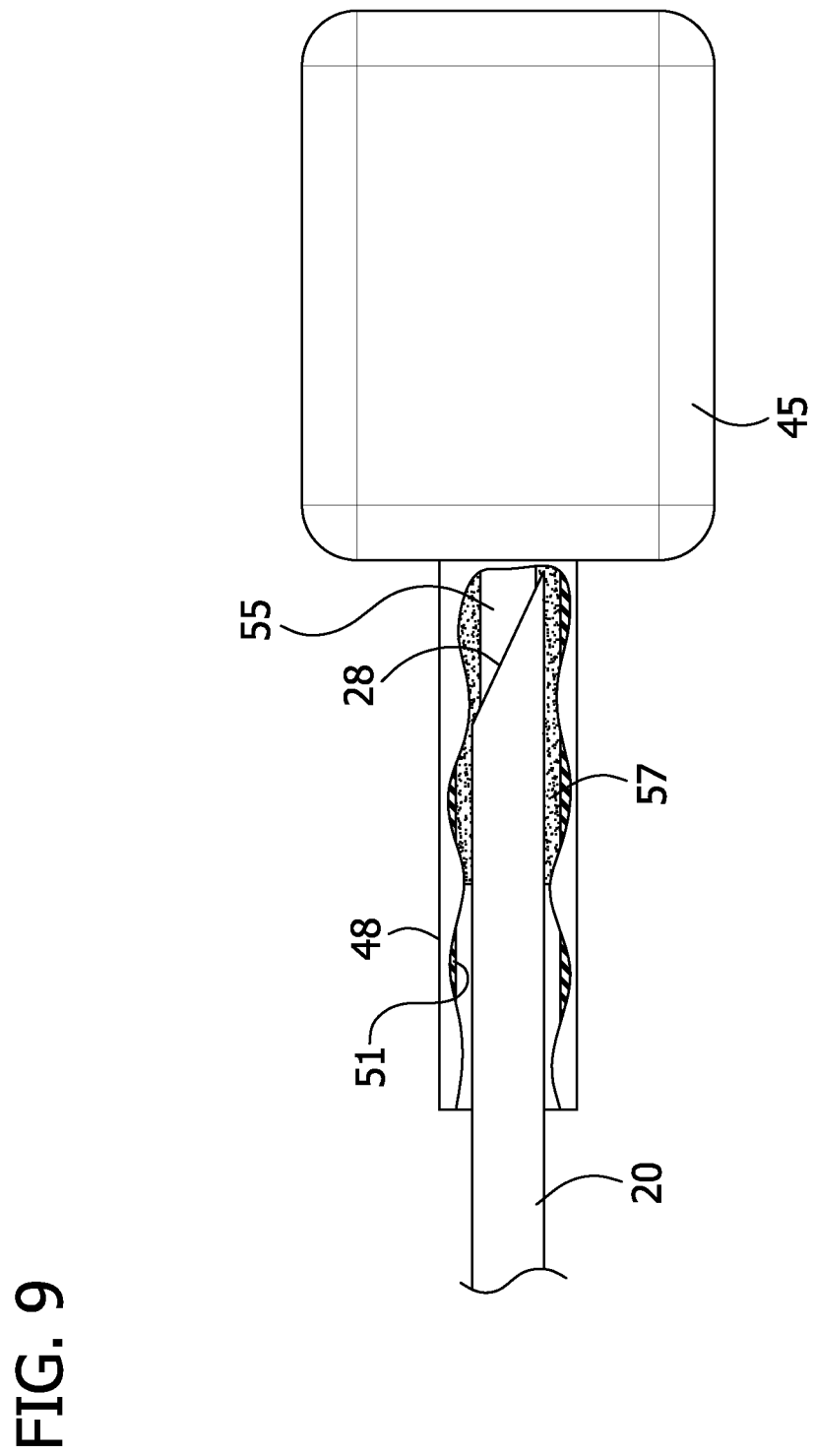
FIG. 9 is an enlarged fragmentary elevation of the needle and shaft of FIG. 8 with parts of the needle broken away.
Figure 10:
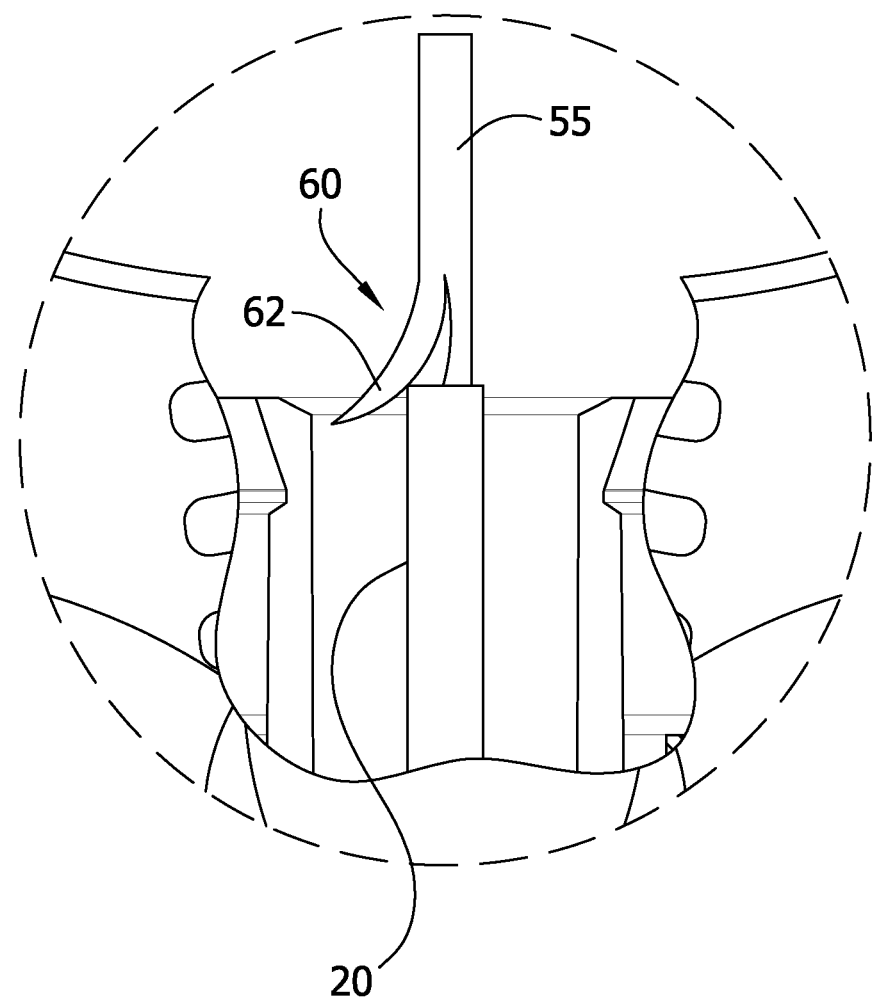
FIG. 10 is an enlarged detail of the distal handle member, cannula and obturator of the needle assembly with parts broken away to illustrate the catch.

Referring to FIGS. 8-10, as the shaft 55 advances in the central axial passage, the tip 28 of the cannula 20 enters the chamber 51 of the shield 48. The tip 28 of the cannula 20 advances in the chamber 51 toward the grip 45 and penetrates into the hematic absorbent body 57 (FIG. 9). The technician continues to advance the shaft 55 until the free end of the flap 62 exits the opening associated with the proximal end of the central axial passage (FIG. 10). As shown in FIG. 8, the free end of the flap 62 preferably does not exit the passage until at least the tip 28 of the cannula 20 is received in the chamber 51 of the shield 48. Also, the flap 62 should exit the opening associated with the proximal end of the passage before the tip 28 of the cannula 29 contacts the closed end of the shield 48.

As shown best in FIG. 10, when the free end of the flap 62 exits the axial passage, it pivots towards the free end of the shaft 55 and into its extended position. In the extended position, the laterally extending flap 62 prevents the shaft 55 from withdrawing from the passage of the cannula 20 because the radial distance D between the free end of the flap and the longitudinal axis of the shaft is greater than the radius of the opening associated with the proximal end of the central axial passage. The flap 62 catches on the edge of the cannula 20 adjacent the opening associated with the proximal end of the central axial passage and cannot move back into the opening. This essentially secures the obturator 26 to the cannula 20. It is envisioned that the flap 62 may engage structure other than the cannula 20 to secure the obturator 26 in place shielding the cannula tip 28. For example, the flap 62 could engage a portion (not shown) of the distal handle member 24.

The flap 62 should be disposed at a location on the shaft 55 of the obturator 26 such that the flap prevents removal of at least the tip 28 of the cannula 20 from the chamber 51 of the shield 48. Thus, the appropriate location of the flap 62 along the length of the shaft 55 depends on the length of the shaft, the length of the passage of the cannula 20 and the length of the chamber 51. Retaining the tip 28 of the cannula 20 within the chamber 51 of the shield 48 prevents the technician and others from being stuck by the tip. There may, and most likely will be, some limited longitudinal movement of the shaft 55 within the central axial passage of the cannula 20. Limited movement is satisfactory as long as at least the tip 28 of the cannula 20 remains within the chamber 51 of the shield 48 while the flap 62 is in the extended position.

In one version of the present invention, the distal handle member 24 and flap 62 are constructed and arranged so that the flap is essentially not accessible when engaged with the distal handle member or cannula 20 at the proximal end of the central axial passageway of the cannula. Therefore, once the flap 62 is engaged, the tip 28 is securely and substantially irreversibly held in the chamber 51 of the shield 48. It is also envisioned that the obturator 26 could be constructed so that it could be removed from the central axial passageway of the cannula 20. For example, if the sample collected in the cannula 20 is not satisfactory it will be necessary to obtain a second sample. This can be done using the same needle assembly 10. To allow a second use, the flap 62 and distal handle member 24 can be configured to permit access to the flap after it is engaged at the proximal end of the central axial passageway of the cannula 20. The technician configures the flap 62 into the retracted position and retains it in such position. For example, the technician may hold the flap 62 in the recess 65 by pressing it down with his or her fingers or any other means by which the flap can be depressed such as a pair of forceps or other suitable instrument. The technician maintains the flap 62 in the retracted position as he or she withdraws the shaft 55 from the cannula passage. Once the free end of the flap 62 enters the opening associated with the proximal end of the central axial passage, it is no longer necessary to hold the flap in the retracted position, and the entire shaft 55 of the obturator can readily be withdrawn from the passage. The assembly 10 is then ready for a second use.

Figure 11:
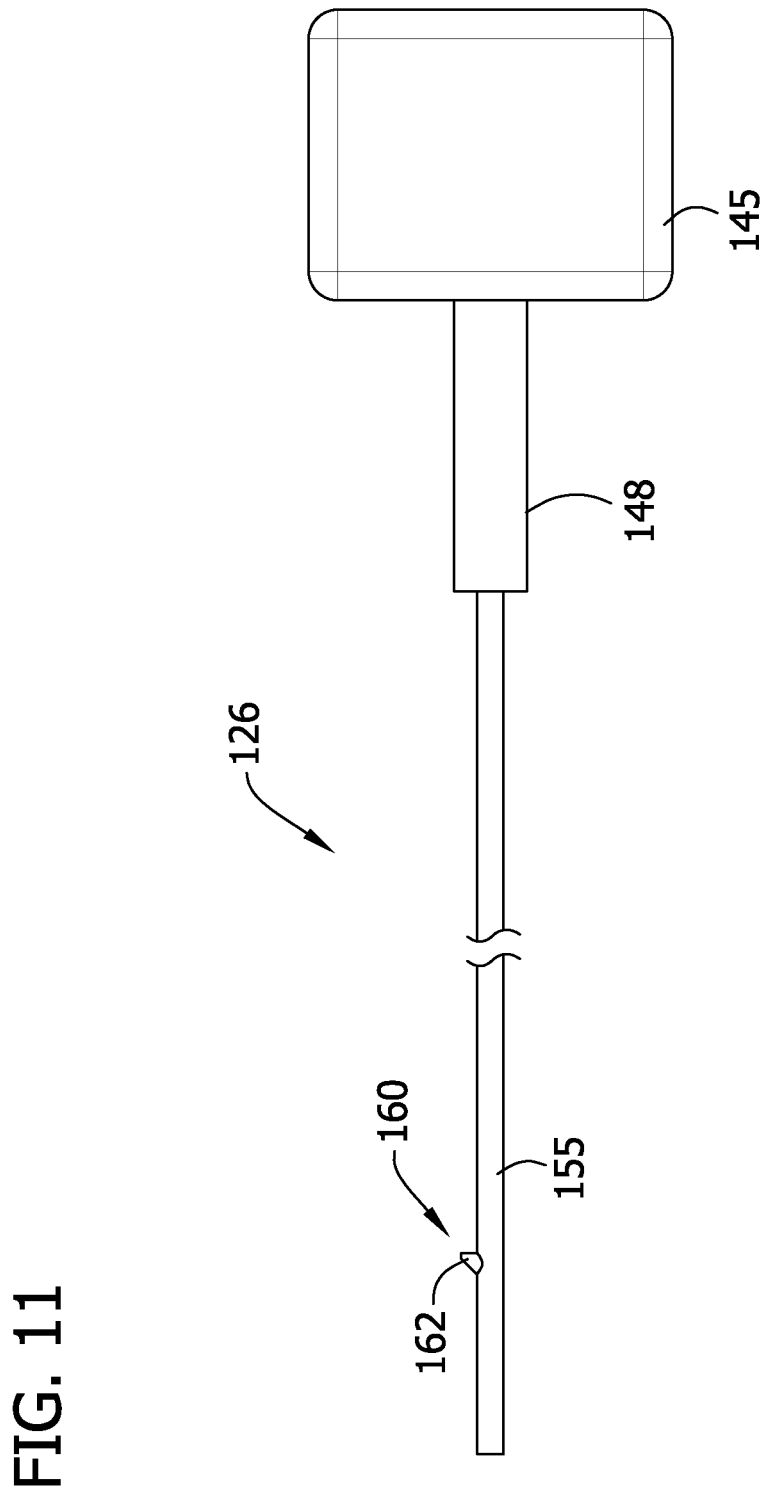
FIG. 11 is a fragmentary elevation of another embodiment of the obturator constructed according to the principles of the present invention.
Figure 12:
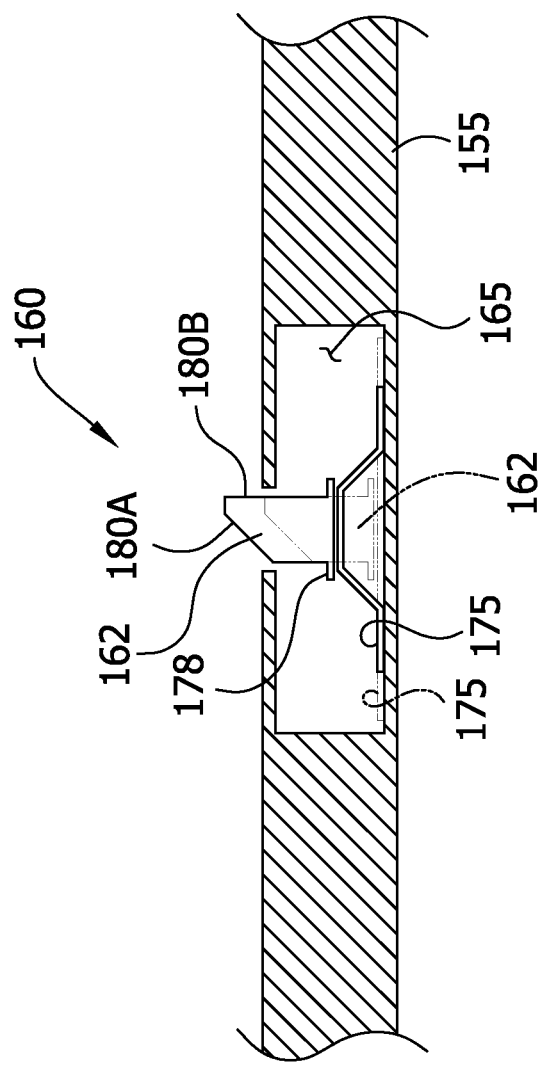
FIG. 12 is a fragmentary longitudinal section of the obturator of FIG. 11.

Referring now to FIGS. 11 and 12, another embodiment a safety device of the present invention is in the form of an obturator and is generally indicated at 126. This embodiment is similar to the previous embodiment of FIGS. 1-10, and as such, corresponding components of the safety device will be indicated by corresponding reference numbers plus "100" for convenience. The difference between this embodiment and the previous embodiment of FIGS. 1-10 is that the catch 160 of the present embodiment comprises an engaging member 162 at least partially received in a cavity 165 formed in the shaft 155 of the obturator 126 (FIG. 12). The engaging member 162 is movable between an extended position, in which a protruding portion of the member extends laterally outward from the cavity 165, and a retracted position in the member is substantially entirely received within the cavity. An outer surface of the protruding portion may be generally flush with the exterior surface of the shaft 155 when the engaging member 162 is in the retracted position. A leaf spring 175 disposed within the cavity 165 biases the engagement member 162 in the extended position. Other types of springs, such as a coil spring, are contemplated. A stop 178 disposed on the engagement member 162 retains a non-protruding portion of the member within the cavity 165. In the illustrated embodiment, the protruding portion of the engagement member 162 has a first face 180A facing the free end of the shaft 155 and an opposite second face 180B facing the grip 145. For reasons discussed below, the first face 180A tapers away from the shaft 155 and the second face 180B extends generally perpendicular to the shaft.

The obturator 126 of the present embodiment is used in substantially the same way as the previous embodiment. In the initial position of the obturator 126, the engagement member 162 is configured in its extended position with the protruding portion of the engagement member extending laterally outward from the cavity 165. The shaft 155 of the obturator 126 is inserted into the passage of the cannula 20 at the tip 28. As the shaft 155 advances in the passage, the first face 180A of the protruding portion of the engagement member 162 contacts the tip 28 of the cannula 28. Because of the tapered first face 180A, the engagement member 162 is forced into the cavity 165, thereby compressing the spring 175. As the shaft 155 advances, the engagement member 162 is forced substantially completely into the cavity 165 (i.e., in the retracted position) and the engagement member enters the passage. The engagement member 162 remains substantially completely within the cavity 165 in the retracted position as the shaft 155 advances within the passage, although a portion of the upper surface of the member may contact the wall of the passage. As with the previous embodiment, the tip 28 of the cannula 20 enters the chamber 151 of the shield 148 and the engagement member 162 exits the passage at the opening associated with the proximal end of the central axial passage. When the engagement member 162 exits, the spring 175 expands forcing the member out of the cavity 165 into the extended position. If the shaft 155 is moved in a direction withdrawing it from the central axial passage, the second face 180B of the engagement member 162 engages the edge of the opening associated with the proximal end of the central axial passage and prevents withdrawal of the obturator 126 from the passage. To disassemble the assembly if, for example a second sample is needed as explained above, the technician forces the engagement member 162 back into the cavity 165 by, for example, pressing the member down with his or her fingers to compress the spring 175. The shaft 155 can then be withdrawn from the passage.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A safety device for shielding a sharp tip of a cannula having an interior passage including first and second opposite ends, the sharp tip being positioned at the first end of the cannula, the safety device comprising:
   a shaft sized and shaped for being received into the passage of the cannula through the first end of the passage and extending to the second end of the passage, the shaft having a first end and a second end;
   a shield supported adjacent the second end of the shaft and constructed for receiving and substantially shielding the sharp tip of the cannula upon reception of the shaft in the cannula passage;
   a catch positioned on the shaft adjacent the first end of the shaft, the catch being adapted to prevent withdrawal of the shaft from the passage of the cannula and withdrawal of the sharp distal tip from within the shield when the shaft is received in the passage in a position where the shield receives the sharp tip of the cannula,the catch mounted on the shaft for the movement between a retracted position in which the catch is substantially aligned with the shaft for movement through the passage of the cannula and an extended position in which the catch projects outwardly from the shaft.

2. The safety device as set forth in claim 1, wherein the catch is biased toward the extended position, said catch being adapted to move to the retracted position as it enters the first end of the passage of the cannula and to move to the extended position as it exits the second end of the passage.

3. The safety device as set forth in claim 2, wherein the catch comprises a flap partially cut longitudinally from the shaft, an associated recess, and a living hinge pivotably connecting the flap to the shaft and biasing the flap toward the extended position.

4. The safety device as set forth in claim 3, wherein the flap is substantially received in the recess when it is in the retracted position.

5. The safety device as set forth in claim 2, wherein the catch comprises an engagement member received in a cavity within the shaft and a spring biasing the engagement member to project outwardly of the cavity and into said extended position, wherein the engagement member is substantially received in the cavity when it is in the retracted position.

6. The safety device as set forth in claim 5, wherein a first face of the engagement member for contacting the tip of the cannula is configured to angle away from the tip as the first face contacts the tip such that the engagement member is forced into the cavity and into the retracted position.

7. The safety device as set forth in claim 1, further comprising an absorbent body disposed within the shield, the absorbent body being positioned to retain fluid from the passage of the cannula within the shield.

8. The safety device as set forth in claim 7, wherein the absorbent body is made of an anti-microbial material.

9. The safety device as set forth in claim 1, wherein the safety device is an obturator for use in removing a sample from the passage of the cannula.

10. The safety device as set forth in claim 1, wherein the shield defines a chamber around the shaft, the chamber extending between an open end of the shield for receiving the sharp distal tip of the cannula and an opposite closed end.

11. The needle assembly for use in collecting a sample of tissue from a patient, the needle assembly comprising:
   a cannula at least partially defining an interior passage including first and second opposite ends, the first end having a sharp tip, the passage being adapted to receive the tissue sample;
   a shaft having a first end and a second end, the first end of the shaft being sized and shaped for being received into the passage of the cannula through the first end of the passage and extending to the second end of the passage for use in removing the sample collected in the cannula from the cannula;
   a shield associated with the second end of the shaft and constructed for receiving and substantially shielding the sharp tip of the cannula upon reception of the shaft in the cannula passage; and
   a catch associated with the shaft, the catch being adapted to engage the needle assembly to prevent withdrawal of the shaft from the passage of the cannula and withdrawal of the sharp distal tip from within the shield when the shaft is received in the passage in a position wherein the shield receives the sharp tip of the cannula, the catch mounted on the shaft for movement between a retracted position in which the catch is substantially aligned with the shaft for movement through the passage of the cannula and an extended position in which the catch projects outwardly from the shaft.

12. The needle assembly as set forth in claim 11, wherein the catch is biased toward the extended position, said catch being adapted to move to the retracted position as it enters the first end of the passage of the cannula and move to the extended position as it exits the second end of the passage.

13. The needle assembly as set forth in claim 12, wherein the catch comprises a flap partially cut longitudinally from the shaft, an associated recess, and a living hinge pivotably connecting the flap to the shaft and biasing the flap toward the extended position.

14. The needle assembly as set forth in claim 13, wherein the flap is substantially received in the recess when it is in the retracted position.

15. The needle assembly as set forth in claim 14, wherein the catch comprises an engagement member received in a cavity within the shaft and a spring biasing the engagement member to project out of the cavity and into said extended position, wherein the engagement member is substantially received in the cavity when it is in the retracted position.

16. The needle assembly as set forth in claim 15, wherein a first face of the engagement member for contacting the tip of the cannula is configured to angle away from the tip as the face contacts the tip such that the engagement member is forced into the cavity and into the retracted position.

17. The needle assembly as set forth in claim 11, further comprising an absorbent body disposed within the shield, the absorbent body being positioned to retain fluid from within the passage of the cannula within the shield.

18. The needle assembly as set forth in claim 17, wherein the absorbent body is made of an anti-microbial material.

19. The needle assembly as set forth in claim 11, wherein the shield defines a chamber around the shaft, the chamber extending between an open end of the shield for receiving the sharp distal tip of the cannula and an opposite closed end.

* * * * *